United States Patent
Ohkoshi

(10) Patent No.: US 10,499,853 B2
(45) Date of Patent: Dec. 10, 2019

(54) SENSOR INSERTING DEVICE AND OPERATING METHOD THEREOF

(71) Applicant: TERUMO KABUSHIKI KAISHA, Shibuya-ku, Tokyo (JP)

(72) Inventor: Takahiro Ohkoshi, Kanagawa (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 301 days.

(21) Appl. No.: 15/592,451

(22) Filed: May 11, 2017

(65) Prior Publication Data

US 2017/0245798 A1 Aug. 31, 2017

Related U.S. Application Data

(60) Division of application No. 14/200,212, filed on Mar. 7, 2014, now Pat. No. 9,662,071, which is a
(Continued)

(30) Foreign Application Priority Data

Sep. 9, 2011 (JP) ................................ 2011-197190

(51) Int. Cl.
*A61B 5/00* (2006.01)
*A61B 5/145* (2006.01)
(Continued)

(52) U.S. Cl.
CPC .......... *A61B 5/6849* (2013.01); *A61B 5/0031* (2013.01); *A61B 5/14503* (2013.01);
(Continued)

(58) Field of Classification Search
None
See application file for complete search history.

(56) References Cited

U.S. PATENT DOCUMENTS

| 5,568,806 A | 10/1996 | Cheney et al. |
| 2006/0020186 A1 | 1/2006 | Brister et al. |

(Continued)

FOREIGN PATENT DOCUMENTS

| CN | 101553176 A | 10/2009 |
| CN | 101686811 A | 3/2010 |

(Continued)

OTHER PUBLICATIONS

The extended European Search Report dated Mar. 26, 2015, by the European Patent Office in corresponding European Patent Application No. 12830074.6-1506. (7 pgs).
(Continued)

*Primary Examiner* — Eric F Winakur
*Assistant Examiner* — Marjan Fardanesh
(74) *Attorney, Agent, or Firm* — Buchanan Ingersoll & Rooney PC

(57) ABSTRACT

A method involves supporting both a sensor which measures biological information and an insertion needle at a location proximally spaced from the distal end portion of a device body. The sensor includes a detector which detects a body fluid component of the patient used to measure the biological information, and a signal processor which is attached to the device body and which processes a signal including the biological information. The method also involves moving the sensor and the insertion needle in the distal direction so that the detector and a portion of the insertion needle protrude distally beyond the distal end portion of the device body, separating the insertion needle from the sensor by moving the insertion needle relative to the sensor toward a proximal direction, and electrically connecting the sensor and the signal processor by operation of the device body after the insertion needle is separated from the sensor.

20 Claims, 19 Drawing Sheets

Related U.S. Application Data continuation of application No. PCT/JP2012/068952, filed on Jul. 26, 2012.

(51) Int. Cl.
*A61B 17/34* (2006.01)
*A61B 5/1486* (2006.01)
*A61M 5/158* (2006.01)

(52) U.S. Cl.
CPC ...... *A61B 5/14532* (2013.01); *A61B 5/14865* (2013.01); *A61B 5/688* (2013.01); *A61B 5/72* (2013.01); *A61B 17/3468* (2013.01); *A61M 5/158* (2013.01); *A61B 2560/063* (2013.01); *A61B 2562/225* (2013.01); *A61M 2005/1585* (2013.01)

(56) References Cited

U.S. PATENT DOCUMENTS

| | | |
|---|---|---|
| 2007/0027381 A1 | 2/2007 | Stafford |
| 2008/0114280 A1 | 5/2008 | Stafford |
| 2008/0249383 A1 | 10/2008 | Sass et al. |
| 2010/0137695 A1 | 6/2010 | Yodfat et al. |

FOREIGN PATENT DOCUMENTS

| | | |
|---|---|---|
| CN | 101808679 A | 8/2010 |
| EP | 2 335 583 A2 | 6/2011 |
| JP | 9-512200 A | 12/1997 |
| JP | 2008-506468 A | 3/2008 |
| WO | 2006/017358 A1 | 2/2006 |
| WO | 2010/091005 A1 | 8/2010 |

OTHER PUBLICATIONS

Office Action (First) dated Apr. 28, 2015, by the Patent Office of the People's Republic of China in corresponding Chinese Patent Application No. 2012800436946 and an English translation thereof of the Office Action. (13 pgs).

Chinese Office Action dated Nov. 4, 2015, by the Chinese Patent Office, in corresponding Chinese Patent Application No. 2012800436946 with English translation. (8 pages).

Communication Pursuant to Article 94(3) EPC issued by the European Office dated May 29, 2018 in corresponding European Patent Application No. 12830074.6 (4 pages).

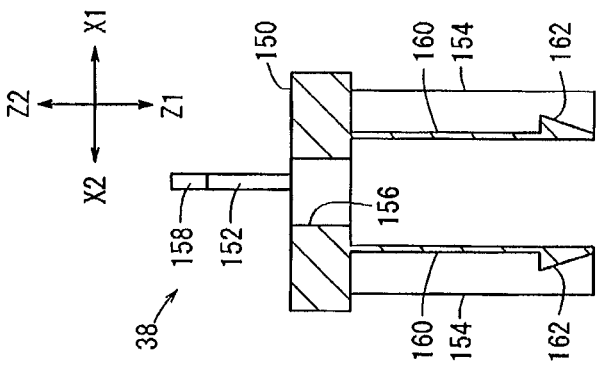
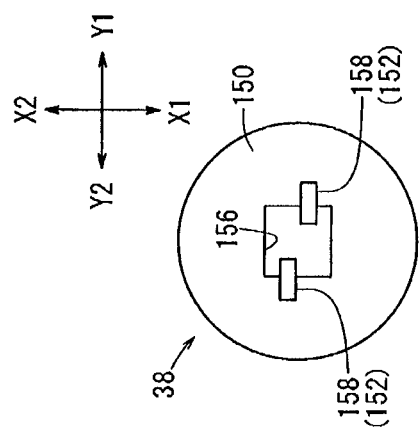
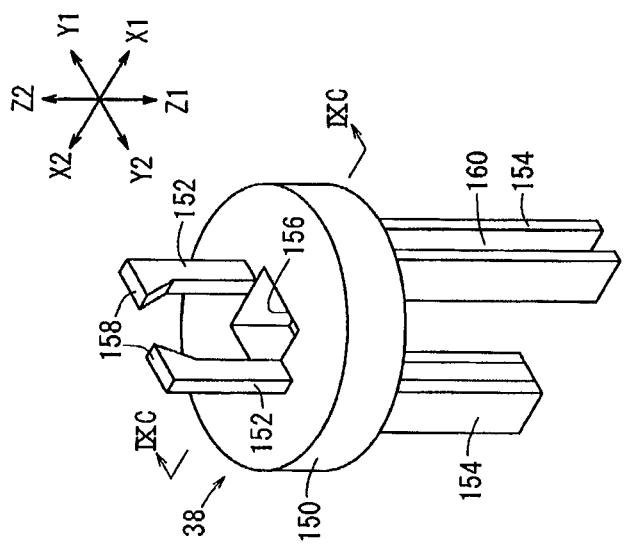

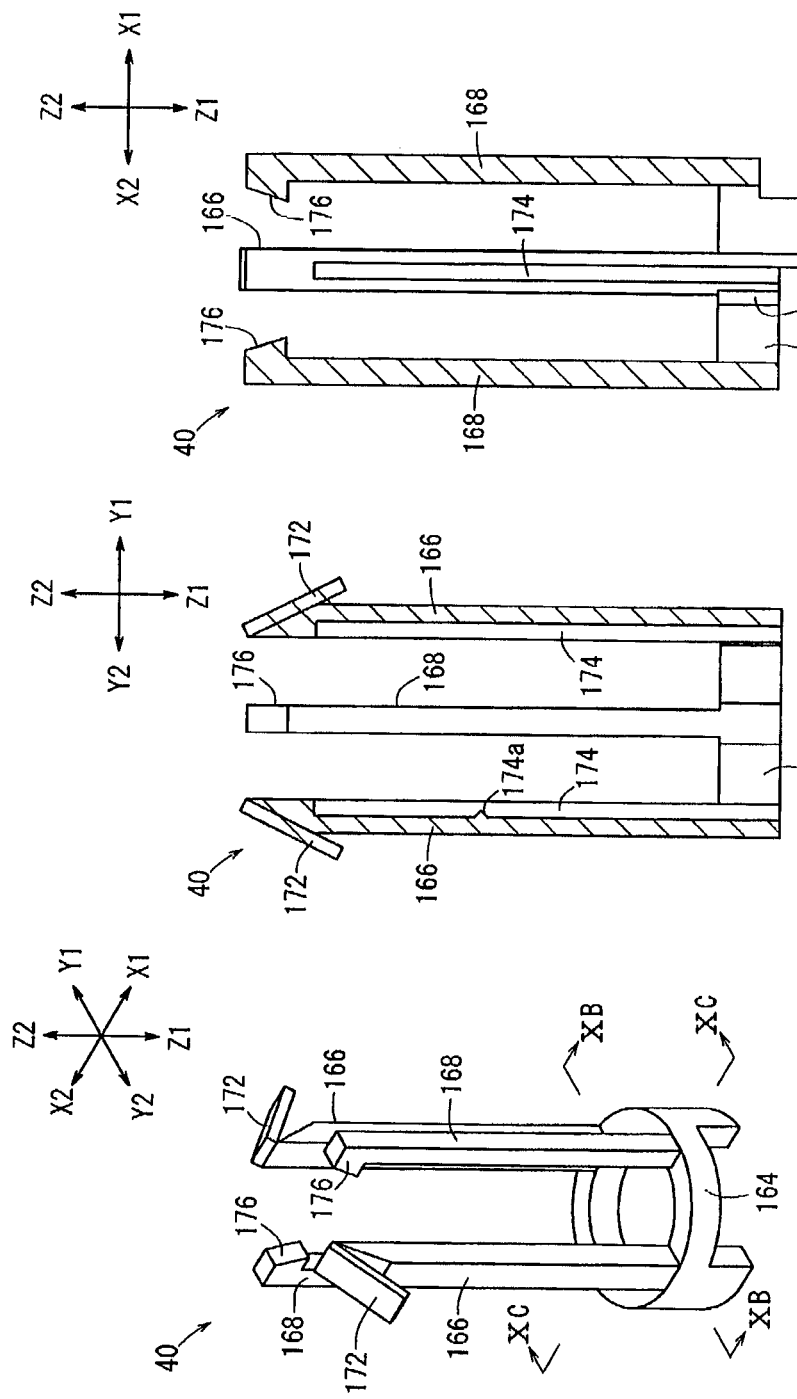

SENSOR INSERTING DEVICE AND OPERATING METHOD THEREOF

CROSS-REFERENCES TO RELATED APPLICATIONS

This application is a divisional of U.S. application Ser. No. 14/200,212 filed on Mar. 7, 2014, which is a continuation of International Application No. PCT/JP2012/068952 filed on Jul. 26, 2012, and claims priority to Japanese Application No. 2011-197190 filed on Sep. 9, 2011, the entire content of all three of which is incorporated herein by reference.

TECHNICAL FIELD

The present invention generally relates to a sensor inserting device for inserting a detector of a sensor which measures biological information of a person to be measured into a body of the person to be measured, and an operating method of the device.

BACKGROUND DISCUSSION

Conventionally, a sensor is inserted or implanted in a body of a patient (person to be measured) to detect an analyte (e.g., glucose or pH, cholesterol, protein, or the like) in blood or body fluid of the patient. In such case, a sensor inserting device is used to penetrate the skin of the patient and to arrange the sensor rapidly and easily (e.g., see JP 2008-506468 Y).

An applicator (sensor inserting device) disclosed in JP 2008-506468 Y includes a needle (insertion needle) which is inserted together with a sensor, a plunger subassembly (movement mechanism) which moves the sensor and the insertion needle for piercing, and an attaching unit (dwelling member) which allows the sensor to dwell on the skin of a patient. Further, an electrode unit (signal processor) having a transmitting function which allows transmitting of obtained information of detected blood sugar level (biological information) to an external medical device is attached to the sensor.

Further, such type of sensor inserting device is used for insertion and dwelling of the sensor in the body of the patient, generally, by steps (an operating procedure) listed below.

1. Attaching a sensor to a sensor inserting device.
2. Releasing a safety mechanism of an insertion needle to allow the insertion needle to move freely.
3. Positioning a dwelling member of the sensor inserting device on a desired location (location of insertion) in a body of a patient, and sticking the dwelling member on to the skin of the patient.
4. Operating the sensor inserting device to insert a detector and the insertion needle in the body of the patient.
5. Separating the sensor inserting device from the patient so that the insertion needle is removed from the sensor, thereby allowing the sensor and the dwelling member to dwell in the body (and on the skin) of the patient.
6. Connecting a signal processor to a sensor portion exposed on the skin of the patient so as to allow the signal processor and the sensor to dwell.

SUMMARY

In an operating procedure of the conventional sensor inserting device, after executing the steps [1] to [5], a user (e.g., a patient) manually connects the sensor and the signal processor in the step [6]. However, when executing the step [6], the sensor dwells on the skin of the patient so that the sufficient stationary state of the sensor is not provided. Further, in the case when the sensor and the signal processor are small sized, it happens that, for example, a precise operation is required for making connection, and this makes the operation of connecting the sensor and the signal processor troublesome, which gives pain to the patient. Particularly, in a case the user is a patient, and when the patient wants to insert, by himself or herself, a sensor in the abdomen (e.g., a flank), one of the arms, or the like, it may be difficult to visually detect the portion to be connected, or the patient may be required to make connection with one hand. Because of such reasons, workability of the operation is deteriorated.

Disclosed here is a sensor inserting device and a method permitting connection of the sensor, which is inserted and allowed to dwell on the skin of a person to be measured, to a signal processor by a relatively simple operation, thereby enabling shortening of the time of operation so that suffering and pain of the person to be measured can be reduced, and an operating method of the sensor inserting device.

According to one aspect, an operating method of a sensor inserting device comprises: supporting both a sensor which measures biological information and an insertion needle at a location proximally spaced a predetermined distance from a distal end portion of a device body of the sensor inserting device, wherein the sensor includes a detector which detects a body fluid component of the patient used to measure the biological information, and the sensor inserting device includes a signal processor which processes a signal including biological information output from the sensor, with the signal processor being attached to the device body; moving the sensor and the insertion needle, which are supported at the location proximally spaced from the distal end portion of the device body, toward a distal end direction so that the detector of the sensor and a portion of the insertion needle protrude distally beyond a distal end portion of the device body; after the detector and the portion of the insertion needle are positioned distally beyond the distal end portion of the device body, separating the insertion needle from the sensor by moving the insertion needle relative to the sensor toward a proximal end direction; and electrically connecting the sensor and the signal processor by operation of the device body after the insertion needle is separated from the sensor.

The detector of the sensor is thus inserted into the body of the person to be measured by the movement mechanism. Connecting the sensor and the signal processor at the location of insertion, the sensor and the signal processor can easily dwell on the skin of the person to be measured. Thereby, the manual operation of connecting the sensor and the signal processor dwelling on the skin of the person to be measured is not necessary. This shortens the operating time of insertion and dwelling of the sensor, and reduces suffering and pain of the person to be measured.

A dwelling member which is arranged on the moving path of the sensor and attached to the sensor by the movement of the sensor caused by the movement mechanism may further be included.

As described above, the sensor inserting device allows the dwelling member to be attached to the sensor by the movement of the sensor caused by the movement mechanism so as the sensor to be supported by the dwelling member without requiring any additional operation. Therefore, the operation of insertion and dwelling of the sensor can further efficiently be carried out.

In this case, the movement mechanism can be configured to movably support the sensor and the insertion needle relative to the device body. The sensor inserting device can be configured to change the state in a manner that: the state changes from the first state in which the sensor and the insertion needle are supported at a location spaced, by a predetermined distance, from a distal end portion of the device body to; a second state in which the dwelling member supports the sensor at the location of insertion, by the sensor and the insertion needle moving toward the distal end direction, with the signal processor attached to the device body, to insert the detector into the body of the person to be measured; after changing to the second state, the state changes to a third state in which the insertion needle is separated from the sensor by the insertion needle moving toward the proximal end direction; and after changing to the third state, the state changes to a fourth state in which the signal processor is connected to the sensor staying at the location of insertion.

As described above, by the changing of the state of the sensor inserting device from the first state to the fourth state, the sensor and the signal processor can easily be connected and allowed to dwell on the skin of the person to be measured. Further, the movement mechanism may include a movable unit which supports the sensor and the insertion needle, an advance spring which gives thrust to the movable unit to move toward the distal end direction of the device body, and a return spring, arranged in a location opposing to the advance spring with the movable unit in between, which moves the insertion needle toward the proximal end direction of the device body.

As described above, by the movable unit supporting the sensor and the insertion needle, and the movable unit moving toward the distal end direction by the advance spring, the state can easily be changed from the first state to the second state (the state in which the detector and the insertion needle are inserted into the body of the person to be measured). Further by the movable unit moving toward the proximal end by the return spring, the state can easily be changed from the second state to the third state (the state in which the insertion needle is separated from the sensor).

Further, the movement mechanism may preferably include a safety mechanism which retains the sensor and the insertion needle in the first state.

By including the safety mechanism for retaining the first state as described above, the sensor inserting device can surely prevent the trouble of piercing the insertion needle by carelessly moving the sensor and the insertion needle toward the distal end direction.

The dwelling member can include an engaging unit which supports the sensor at the location of insertion, a base which supports the state in which the supported sensor is connected to the signal processor, and an adhesive portion which sticks the base on to the skin of the person to be measured.

In this manner, the sensor is supported by the engaging unit and the sensor is supported in a state connected to the signal processor so that the connection between the sensor and the signal processor on the skin of the patient can further firmly be retained, thereby allowing stable and continuous detection of biological information by the sensor.

Further, on the distal end portion of the device body, the dwelling member may be arranged, and also, a signal processor displacement mechanism which allows the signal processor to slide toward the base so as to be supported by the dwelling member after the detector is inserted into the body of the person to be measured may be provided.

By the signal processor displacement mechanism allowing the signal processor to slide toward the base so as to be supported by the dwelling member as in such manner, for example, even when the signal processor is arranged in a manner to move in the direction different from that of the movement of the sensor, the sensor and the signal processor can easily be connected at the location of insertion.

In this case, a push handle which can be displaced by two stages toward the distal end direction of the device body may be provided. It may be configured that the push handle operates the movement mechanism by a first stage displacement to insert the detector and the insertion needle into the body of the person to be measured, and after the first stage displacement, the push handle operates the signal processor displacement mechanism by a second displacement to slide the signal processor.

As described above, by operating the push handle which can be displaced by two stages toward the distal end direction of the device body, the detector and the insertion needle are inserted and the signal processor is made to slide (that is, the signal processor is supported by the dwelling member) so that the sensor and the signal processor are easily connected and allowed to dwell.

Further, the engaging unit is an engaging plate which stands upright against the sensor and engages with the sensor when the sensor comes to the location of insertion. And after engaging with the sensor, the engaging plate may preferably be made to fall down by making contact with the signal processor, by the sliding of the signal processor, thereby making electrical connection between the sensor and the signal processor.

In this manner, the sensor and the signal processor can be connected further firmly and allowed to dwell, thereby allowing the signal processor to surely process biological information detected by the sensor.

Further, the device body includes a guiding member which guides the movement of the sensor. The guiding member may be configured to support the engaging plate in the upright position when the sensor moves, and to cancel supporting of the engaging plate in the upright position when the sensor is engaged. In this manner, the sensor and the engaging plate are firmly engaged with the engaging plate kept in the upright position, thereby supporting the sensor in the dwelling member.

According to another aspect, an operation method may involve the following first to fourth steps. In the first step, the sensor which measures biological information and the insertion needle are supported at the location spaced, by a predetermined distance, from the distal end portion of the device body of the sensor inserting device, and a signal processor which processes a signal including biological information output from the sensor is attached to the device body. In the second step, after the first step, the movement mechanism provided in the device body moves the sensor and the insertion needle toward the distal end direction to allow the detector of the sensor and a portion of the insertion needle to protrude from the distal end portion of the device body. In the third step, after the second step, the insertion needle is separated from the sensor by moving the insertion needle toward the proximal end direction. In the fourth step, after the third step, the device body is operated to connect the sensor to the signal processor. In this manner, the sensor and the signal processor can be connected by a simple operation of the device.

According to another aspect, a method comprises: moving a sensor inserting device toward skin of a living body, wherein the sensor inserting device comprises an insertion needle, a sensor which measures biological information and outputs the biological information, and a signal processor, with the moving of the sensor inserting device toward the skin of the living body including moving the insertion needle, the sensor and the signal processor toward the skin of the living body; positioning a distal end of a sensor inserting device against the skin of the living body, with the needle possessing a distal end that is proximally spaced from the distal end of the sensor inserting device when the distal end of the sensor inserting device is initially positioned against the skin of the living body, the sensor including a detector which detects a body fluid component of the living body used to measure the biological information; and moving both the sensor and the insertion needle toward the skin of the living body to cause the distal end of the insertion needle to puncture the skin of the living body, the movement of the sensor resulting in movement of the detector to position at least a part of the detector in the skin of the living body. During the moving of both the sensor and the insertion needle toward the skin of the living body, the sensor is electrically disconnected from the signal processor which processes the biological information output from the sensor. The method further comprises; after the puncturing of the skin of the living body, moving the insertion needle away from the skin of the living body to remove the distal end of the insertion needle from the skin of the living body while keeping the at least a part of the detector in the skin of the living body; and electrically connecting, after the insertion needle is removed from the skin of the living body, the sensor to the signal processor which processes the biological information output from the sensor.

According to the disclosure here, the sensor which is inserted to dwell on the skin of the person to be measured and the signal processor can be connected by a simple operation of the device so that the operating time can be shortened, thereby reducing the suffering and pain of the person to be measured.

BRIEF DESCRIPTION OF DRAWINGS

FIG. 9A is a perspective view in which the fixing member in FIG. 3 is enlarged, FIG. 9B is a plan view of the fixing member in FIG. 3, and FIG. 9C is a cross-sectional view taken along the section line IXC-IXC in FIG. 9A.

FIG. 10A is a perspective view of the guiding member in FIG. 3, FIG. 10B is a cross-sectional view taken along the section line XB-XB in FIG. 10A, and FIG. 10C is a cross-sectional view taken along the section line XC-XC in FIG. 10A.

DETAILED DESCRIPTION

An embodiment of a sensor inserting device and an operating method of the device, representing examples of the device and method disclosed here, will be described in detail below referring to the accompanying drawings.

Figure 1:
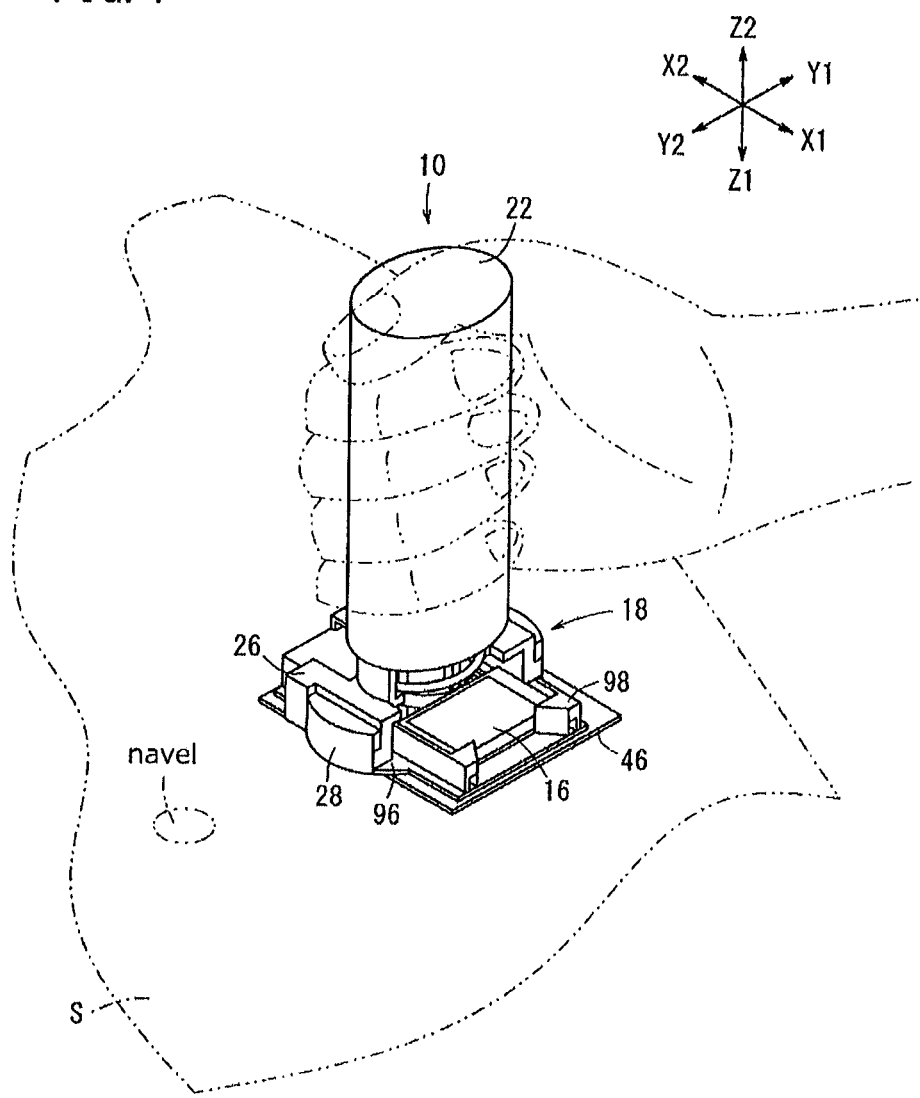
FIG. 1 is a perspective view schematically illustrating a state in which a sensor inserting device according to an embodiment disclosed here is used.
Figure 2:
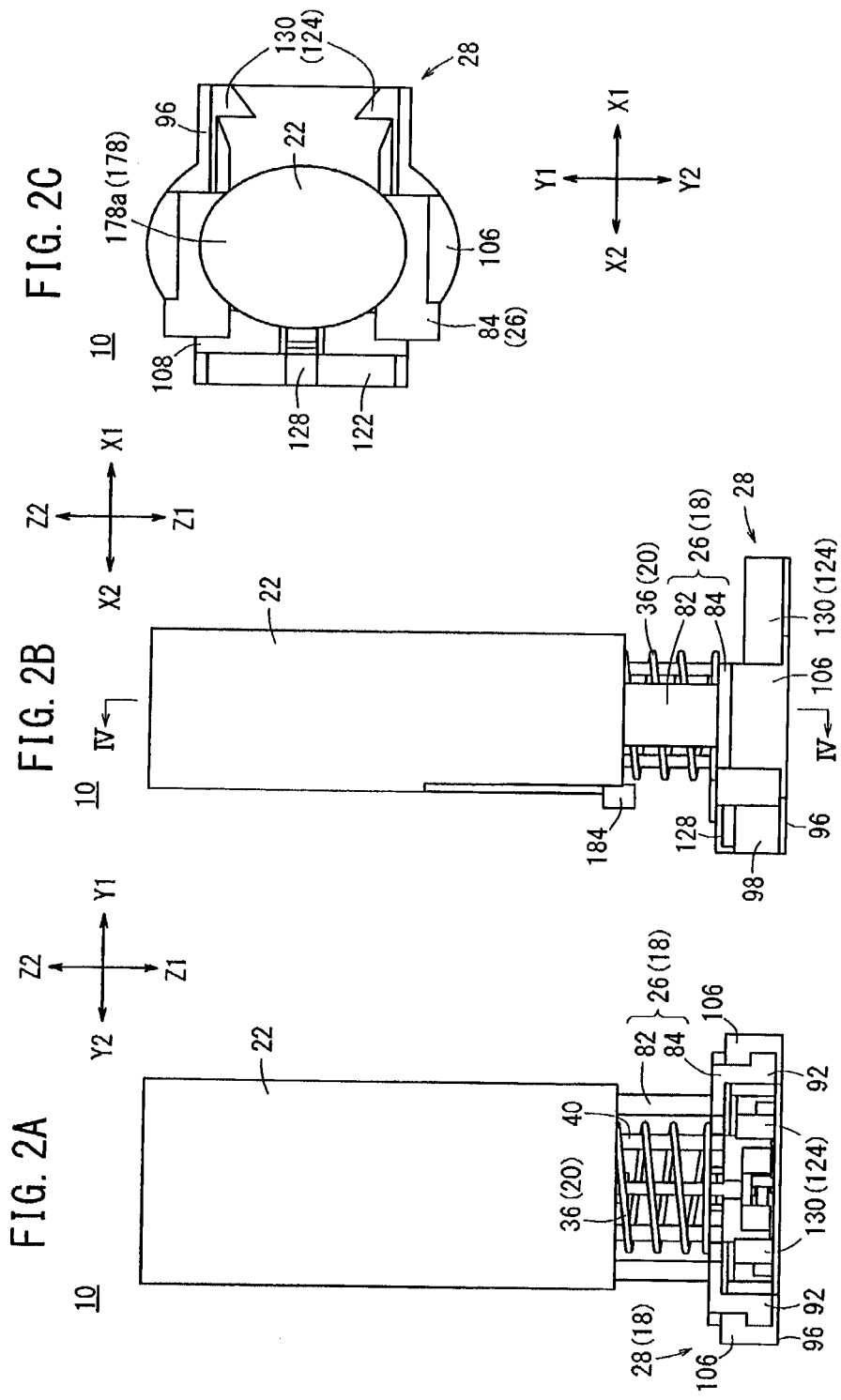
FIG. 2A is a front view of the sensor inserting device in FIG. 1.
FIG. 2B is a side view of the sensor inserting device in FIG. 1.
FIG. 2C is a plan view of the sensor inserting device.

The sensor inserting device 10 disclosed here is a device, as illustrated in FIG. 1, for carrying out a predetermined operation at a suitable location on a skin S of a patient (person to be measured), for example, an unobtrusive portion where the body motion is small, such as an abdomen, so as to insert a detector 14 (see FIG. 3) of a sensor 12 into the body of the patient, connect a connecting portion of the sensor exposed on the skin S to a transmitter (signal processor) 16, and allow the sensor 12 and the transmitter 16 to dwell on the skin S.

Note that, in the description below, based on the illustration of the sensor inserting device 10 in FIG. 1, the front-and-rear direction of the device is referred to as the X direction, the right-and-left width direction of the device is referred to as the Y direction, and the height direction of the device is referred to as the Z direction (up-and-down direction). Further, the downward direction of the sensor inserting device 10 is also referred to as the distal end direction or Z1 direction and the upward direction of the sensor inserting device 10 is also referred to as the proximal end direction or Z2 direction. Further, the forward direction and the rearward direction of the sensor inserting device 10 are also referred to as the X1 direction and the X2 direction, respectively, and the rightward direction and the leftward direction of the sensor inserting device 10 are also referred to as the Y1 direction and the Y2 direction, respectively. These directions are used for convenience of description, and therefore, it goes without saying that the sensor inserting device 10 can be used in any direction.

As illustrated in FIG. 1 to FIG. 4, the sensor inserting device 10 includes a device body 18, a movement mechanism 20 which inserts the detector 14 of the sensor 12 into the body of a patient, a push handle 22 for operating the movement mechanism 20, and a dwelling member 24 which dwells, with the sensor 12, on the skin S of the patient (note that, in FIG. 2A to 2C and FIG. 4, illustrations of the transmitter 16 and the dwelling member 24 are omitted for ease of understanding of the drawings).

The device body 18 includes a housing 26 extending in the up-and-down direction (Z direction) and a slider mechanism (signal processor displacement mechanism) 28 attached to the distal end portion (lower portion) of the housing 26.

Figure 3:
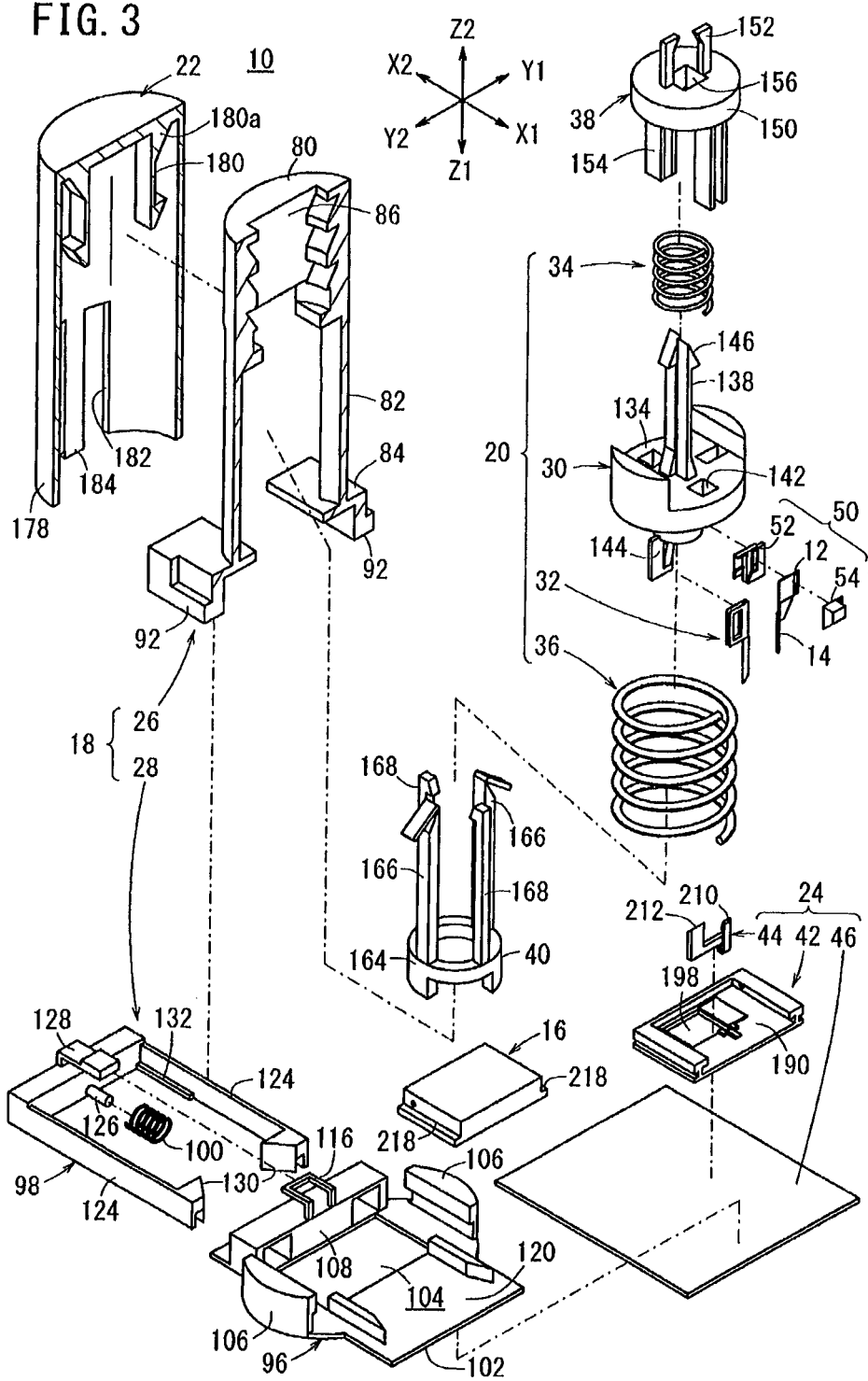
FIG. 3 is an exploded perspective view of the sensor inserting device in FIG. 1.

As illustrated in FIG. 3, the movement mechanism 20 includes a head (movable unit) 30 which is contained inside the housing 26 and movable in the Z direction, an insertion needle 32 attached to the distal end portion of the head 30, an advance spring 34 which presses the head 30 toward the distal end direction (Z1 direction), and a return spring 36 which presses the head 30 toward the proximal end direction (Z2 direction). Further, the device body 18 is provided with a fixing member 38 which supports the head 30 at a predetermined height in the device body 18 before the inserting operation of the sensor 12 and the insertion needle 32 (movement of the head 30) and a guiding member (guide member) 40 which guides the sensor 12 and the insertion needle 32 during the inserting operation.

Further, the push handle 22 is attached so as to cover the upper side of the housing 26 and be movable toward the distal end direction by an operation of a user. Further, the dwelling member 24 includes a base (base portion) 42 arranged in the slider mechanism 28, an engaging arm (engaging plate) 44 pivotally engaged with the base 42, and an adhesive sheet 46 (adhesive portion) adhering to the bottom surface (distal end surface) of the base 42.

The sensor inserting device 10 according to this embodiment disclosed by way of example allows the components mentioned above to work together with each other so that the sensor 12 (detector 14) is inserted, rather rapidly and securely, into the body through the skin S of the patient, and after the insertion, the sensor 12 is relatively easily connected to the transmitter 16 which are then allowed to dwell on the skin S of the patient. The sensor 12 which is inserted into the body of the patient by the sensor inserting device 10 detects information about glucose concentration (biological information) included in body fluid of the patient. The detected information about glucose concentration is automatically (or by an operation) transmitted wirelessly via the transmitter 16 to external medical equipment (e.g., a display or an electronic medical record) to be used for managing blood sugar level of the patient.

The subject to which the sensor inserting device 10 carries out insertion is not limited to the sensor 12 for detecting the blood sugar level. For example, the device can be applied to various objects such as insertion and dwelling of a sensor for detecting pH and cholesterol, protein, or the like as the biological information other than the blood sugar level.

In the illustrated embodiment, the sensor 12 which detects the blood sugar level of the patient is configured as a unit. The sensor unit 50 is configured with three components, that is, the sensor 12, an engaging member 52, and a connecting member 54.

Figure 5:
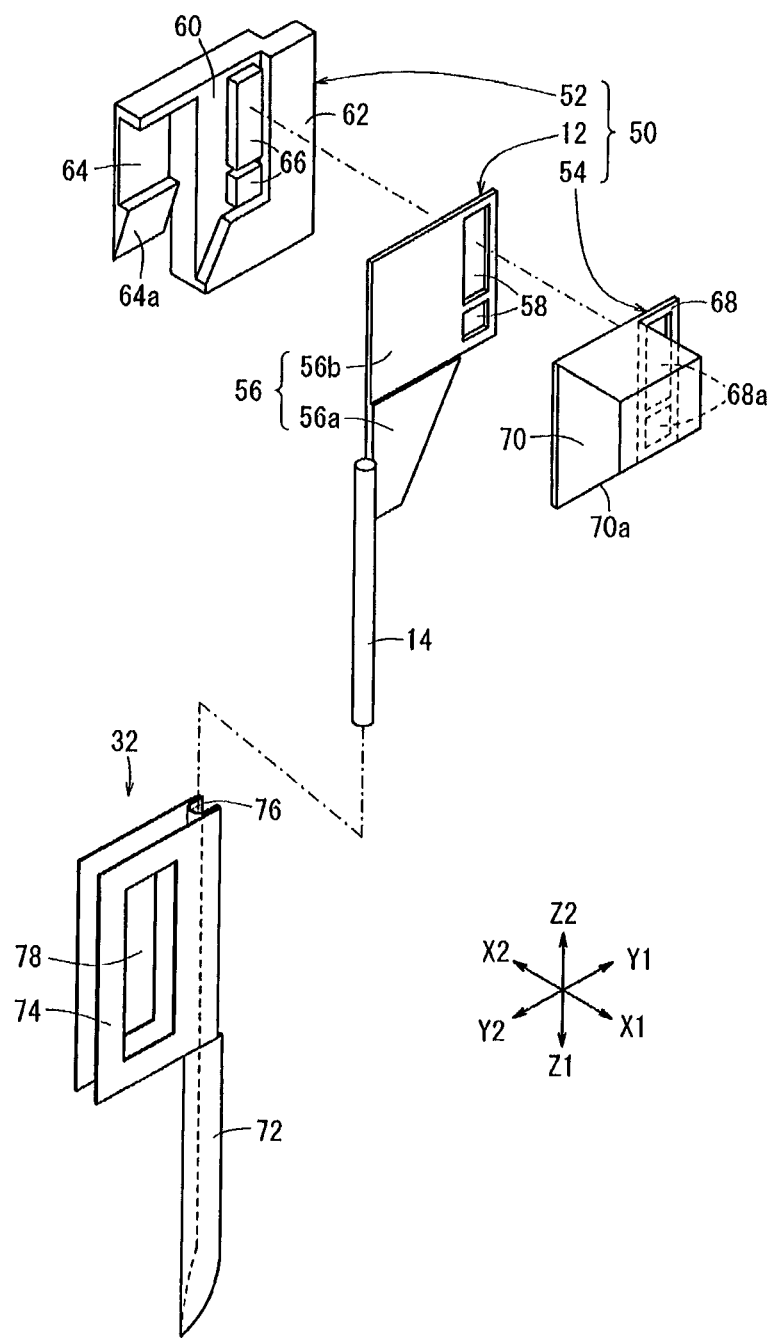
FIG. 5 is a perspective view in which the sensor unit and the insertion needle in FIG. 3 are enlarged.

FIG. 5 illustrates the sensor unit 50 and the insertion needle 32 in an enlarged manner. As illustrated in FIG. 5, the sensor 12 includes the detector 14 which is inserted into the body of the patient to detect a body fluid component of the patient and a sensor base 56 exposed on the skin S of the patient when the detector 14 is inserted in the body of the patient.

As for measuring the glucose concentration in the body fluid component by the sensor 12, a well-known measurement method can be applied. For example, an enzyme method using a glucose oxidase electrode (GOD) is one possibility. In this case, the detector 14 is configured with an oxidation-reduction electrode including an enzyme which reacts with blood sugar (e.g., glucose oxidase and glucose dehydrogenase).

When the blood makes contact with the detector 14 and a reaction between the blood and an enzyme takes place, the glucose (blood sugar) is decomposed into gluconic acid and hydrogen peroxide, and the hydrogen peroxide is decomposed into water and an electron. By detecting the electron thus produced, the glucose concentration in the blood, that is, the blood sugar level can be calculated based on the current value. The configuration of the sensor 12 (detector 14) is not limited to the configuration described above. For example, a configuration may be employed using a fluorescent pigment which produces or reduces fluorescent light by coupling with glucose. The sensor 12 can suitably be selected among various types according to an analyte component.

The detector 14 may preferably have flexibility so as that the detector 14 can rather easily be inserted into the living body of the patient and damage to a living body tissue can be reduced. Further, the length of the detector 14 may preferably be, for example, 0.2 to 10 mm when insertion is carried out into the body of the patient. The length also depends on a subject to which insertion is carried out (a blood vessel or a living body tissue) or a location of insertion.

Contrary to the detector 14 inserted underneath the skin of the patient, the sensor base 56 is a component exposed on the skin S, that is the sensor base 56 is exposed outside the body. The sensor base 56 includes a connecting portion 56a to which the detector 14 is connected to be in the distal end (Z1 direction) side and a proximal end portion 56b continuously connected to the connecting portion 56a and possessing an approximately square shape. The connecting portion 56a is configured to have flexibility so as to allow the sensor base 56 (proximal end portion 56b) to bend in the front-and-rear direction against the detector 14. The proximal end portion 56b is configured as a connecting surface of the engaging member 52 and the connecting member 54. On a right side surface of the proximal end portion 56b, hook holes 58 are formed to have two different types of rectangular shapes (a rectangle and a square).

The engaging member 52 is a plate-like member having a predetermined thickness. One of the sides of the engaging member 52 is formed to have a shape partially overlapping with the sensor base 56. Specifically, the engaging member 52 includes a sensor arrangement portion 60 on which a portion of the sensor base 56 is arranged, a sensor side guiding portion 62, and a sensor side hook 64.

The sensor arrangement portion 60 is located in an approximately middle portion of the Y direction of the engaging member 52. On the surface of the sensor arrangement portion 60, two types of sensor retaining protrusions 66 which engage with two types of hook holes 58 of the sensor base 56 are protrudingly formed. That is, the two types of sensor retaining protrusions 66 protrude away from the surface of the sensor arrangement portion 60. The sensor base 56 is arranged on the surface of the sensor arrangement portion 60 so that the sensor retaining protrusions 66 penetrate (are positioned in) and engage with the hook holes 58, and thereby the engaging member 52 is attached and fixed to the sensor 12.

The sensor side guiding portion 62 is located in the right (Y1 direction) side of the sensor arrangement portion 60 and extends toward the Z direction with a thickness smaller than the sensor arrangement portion 60. The sensor side guiding portion 62 is arranged so as to allow guiding by the guiding member 40 (see FIG. 3).

The sensor side hook 64 is arranged in the left (Y2 direction) side of the sensor arrangement portion 60. The upper portion (proximal end portion) of the sensor side hook 64 is connected to the side surface of the sensor arrangement portion 60, by which the whole sensor side hook 64 is supported. The distal end portion of the sensor side hook 64 is flexibly swingable against the connecting portion of the proximal end portion. A forwardly protruding hook 64a is provided on the distal end portion of the sensor side hook 64, and the hook 64a is engaged with the engaging arm 44 (see FIG. 3) of the dwelling member 24.

The connecting member 54 is a member which is layered on or overlies the surface of the sensor base 56 of the sensor 12, and includes, in a plan view, a sensor connecting portion 68 formed in the Y1 direction and a sensor side connecting terminal 70 formed in the Y2 direction.

The sensor connecting portion 68 includes a hook hole 68a which has a shape same as that of the hook hole 58 of the sensor base 56. That is, the sensor unit 50 is integrated as a unit by the engaging member 52, the sensor 12, and the connecting member 54 layered or overlying one another in this order, and the sensor retaining protrusion 66 of the engaging member 52 penetrating (positioned in), and engaging with, each of the hook holes 58 and 68a of the sensor 12 and the connecting member 54, respectively.

The sensor side connecting terminal 70 possesses a trapezoidal shape in which the thickness is greater at the proximal end side and taperingly decreases from approximately the middle portion toward the distal end side. On the tapered surface 70a, a conductive terminal which is electrically connectable to the transmitter 16 is provided. When the sensor 12, the engaging member 52, and the connecting member 54 are integrated as in the manner mentioned above (that is, when the sensor 12 and the connecting member 54 are layered or positioned in an overlying or overlapping relationship), the contact surface of the connecting member 54 and the sensor base 56 becomes electrically conductive so that the sensor unit 50 can transmit the blood sugar level (current value) detected by the detector 14 to the connecting member 54.

The sensor unit 50 is attached to the insertion needle 32, and contained and supported inside the device body 18 of the sensor inserting device 10. The insertion needle 32 is fabricated from a rigid metal material (e.g., stainless steel) so as to easily pierce the skin S of the patient. The insertion needle 32 includes a needle portion 72 extending toward the distal end (Z1 direction) side and an airfoil portion 74 formed in the proximal end (Z2 direction) side of the needle portion 72.

Further, the needle portion 72 and the airfoil portion 74 of the insertion needle 32 according to the embodiment are integrally formed by folding a thin metal sheet inward using any suitable forming method (e.g., press forming). In this manner, sufficient strength can be provided, even for a relatively thin metal sheet material, for the insertion needle 32, and also, reduction in production cost can be expected.

The needle portion 72 possesses an acute angle so as to easily pierce the skin S by cutting a portion of the distal end portion of the needle portion 72. By folding the metal material inward, the needle portion 72 possesses an arc-shape cross section with an opening on the side facing the Y1 direction. The inner surface of the arc-shape extends along the axial direction to form an insertion needle side groove 76. The insertion needle side groove 76 extends from the distal end to the proximal end of the insertion needle 32 including the airfoil portion 74 and temporary holds the detector 14 of the sensor 12.

The airfoil portion 74 is a rectangular component in which the thin sheet metal material is folded in the direction opposite to that of the insertion needle side groove 76. The airfoil portion 74 is formed to have two (a pair of) overlapping airfoil portions 74. The pair of airfoil portions 74 extends toward the Y2 direction with a space, between each other, approximately the same as the thickness of the head side support plate 144 (see FIG. 3) of the head 30. Further, on each plane portion of the pair of airfoil portions 74, a rectangular insertion needle side attaching hole 78 is drilled.

Figure 4:
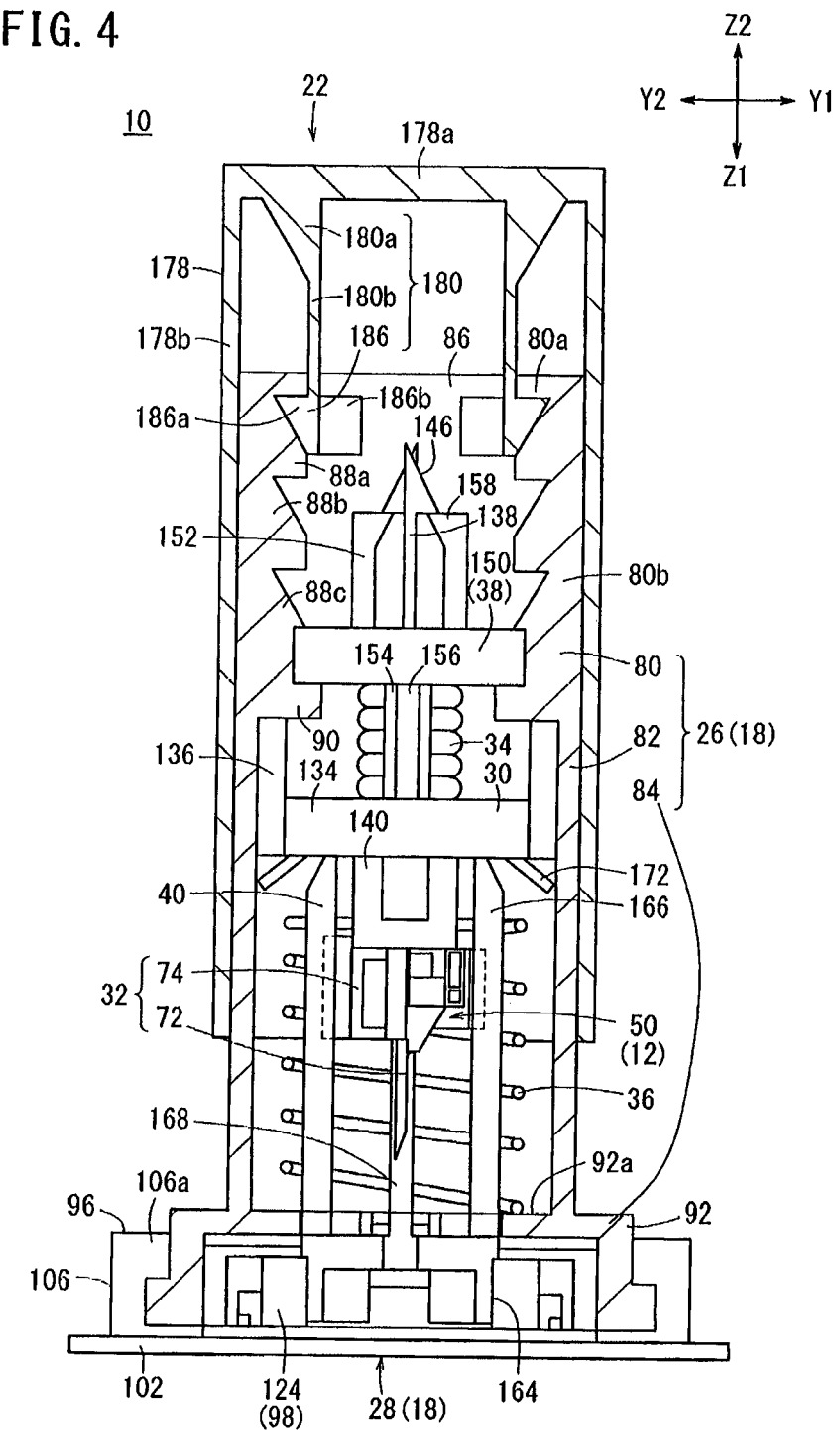
FIG. 4 is a cross-sectional view of the sensor inserting device in FIG. 2B taken along the section line IV-IV.

As illustrated in FIG. 4 and FIG. 5, the insertion needle 32 is supported in the device body 18 with the sensor unit 50 temporarily held in the insertion needle side groove 76. The sensor inserting device 10 carries out insertion (piercing) of the detector 14 and the insertion needle 32 into the body of the patient by the movement, caused by the movement mechanism 20, of the sensor unit 50 and the insertion needle 32 in the distal end direction (Z1 direction). Now, each component of the sensor inserting device 10 which carries out insertion of the sensor unit 50 and the insertion needle 32 will specifically be described.

Figure 6A:
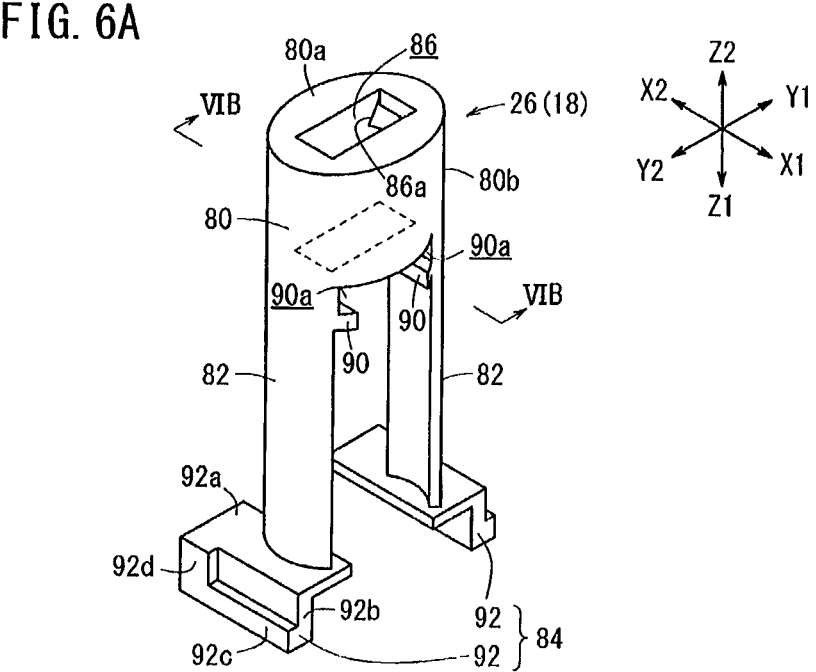
FIG. 6A is a perspective view illustrating an overall configuration of the hosing in FIG. 3
Figure 6B:
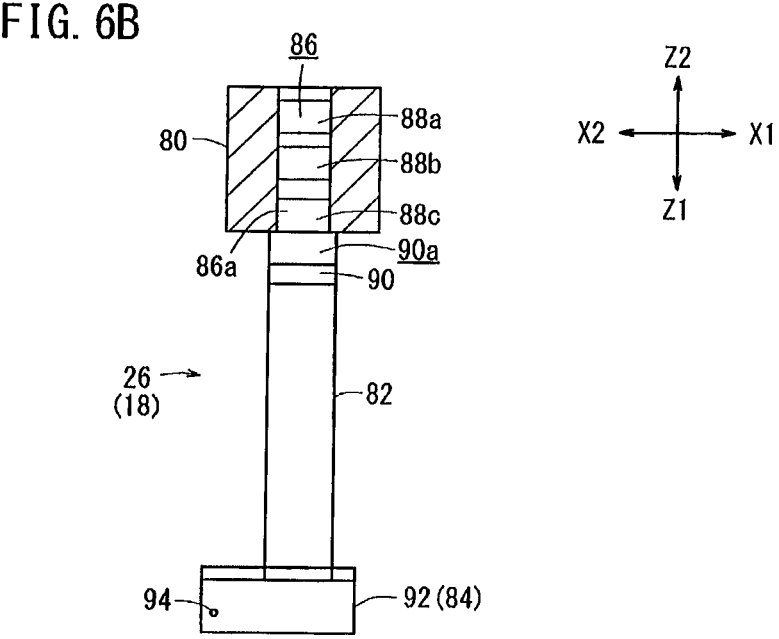
FIG. 6B is a cross-sectional view taken along the section line VIB-VIB in FIG. 6A.

As illustrated in FIG. 6A and FIG. 6B, the housing 26 extends in the up-and-down direction (Z direction) and constitutes a frame of the sensor inserting device 10. The housing 26 is preferably made of a resin material having relatively high rigidity so that the movement mechanism 20, the fixing member 38, and the guiding member 40 (see FIG. 3) can be supported inside the frame. In the housing 26, a proximal end cylindrical portion 80, an extending portion 82, and a distal end attachment portion 84 are formed in this order from the top side toward the bottom side.

The proximal end cylindrical portion 80 of the housing 26 possesses a bottomed cylindrical shape having an upper bottom portion 80a having an elliptical shape, in a plan view, constituting an upper end of the housing 26 and a side circumferential portion 80b extending from the rim of the upper bottom portion 80a toward the distal end side. In the proximal end cylindrical portion 80, the upper bottom portion 80a and the side circumferential portion 80b surround an internal space 86 having an approximately rectangular shape, in a plan view, penetrating the proximal end cylindrical portion 80 in the up-and-down direction. An operating bar 180 (FIG. 3) of the push handle 22 is contained in the internal space 86 via a top surface opening of the upper bottom portion 80a. Further, in the proximal end cylindrical portion 80, the inner surface of a pair of inner walls 86a covering the width direction (Y direction) side of the internal space 86 possesses a rack shape (see FIG. 3, etc.). Specifically, each of the pair of inner walls 86a has three stages of a tooth 88 (i.e., each of the inner walls possesses three teeth). In each stage, the thickness of the tooth 88 taperingly increases from the proximal end side toward the distal end side (hereinafter, each tooth is referred to as, from the proximal end side, a first tooth 88a, a second tooth 88b, and a third tooth 88c).

The pair of extending portions 82 of the housing 26 is provided on the side circumferential portion 80b of the proximal end cylindrical portion 80 in the major axis (Y direction) sides of the elliptical shape. The pair of extending portions 82 extends toward the distal end direction by a predetermined distance, and the distal end attachment portion 84 is formed on the distal end portion of the extending portion 82. The extending portion 82 possesses an arc-shape cross section corresponding to the side circumferential portion 80b of the proximal end cylindrical portion 80, thereby providing sufficient rigidity. Further, the extending portion 82 has a pair of proximal end side protruding portions 90 protruding inward at a location spaced, by a predetermined distance, from the distal end surface of the proximal end cylindrical portion 80. Therefore, a gap 90a having a predetermined space exists between the distal end surface of the proximal end cylindrical portion 80 and the top surfaces of the pair of proximal end side protruding portions 90. The fixing member 38 (see FIG. 3) is arranged in the gap 90a.

The distal end attachment portion 84 of the housing 26 is a component which is attached to, and supports, the slider mechanism 28 (see FIG. 3). The distal end attachment portion 84 is configured with a pair of attachment arms 92 continuously connected to the distal end portion of the pair of extending portions 82 and extending in the front-and-rear direction (X direction). Each attachment arm 92 includes an upper plate 92a extending in the front-and-rear direction and the width direction from the extending portion 82, a side plate 92b extending from the outer edge of the upper plate 92a toward the distal end side, an engaging plate 92c extending further outward from the side plate 92b, and a longitudinal plate 92d perpendicular to the engaging plate 92c at the rear side of the side plate 92b. The adjacent plates stiffen each other so that the rigidity of the attachment arm 92 is improved. The pair of attachment arms 92 is provided with a housing side recess 94 (see FIG. 6B) at a predetermined location in the inner surface of the side plate 92b (in the rear side and approximately in the middle portion in the up-and-down direction of the side plate 92b).

Figure 7:
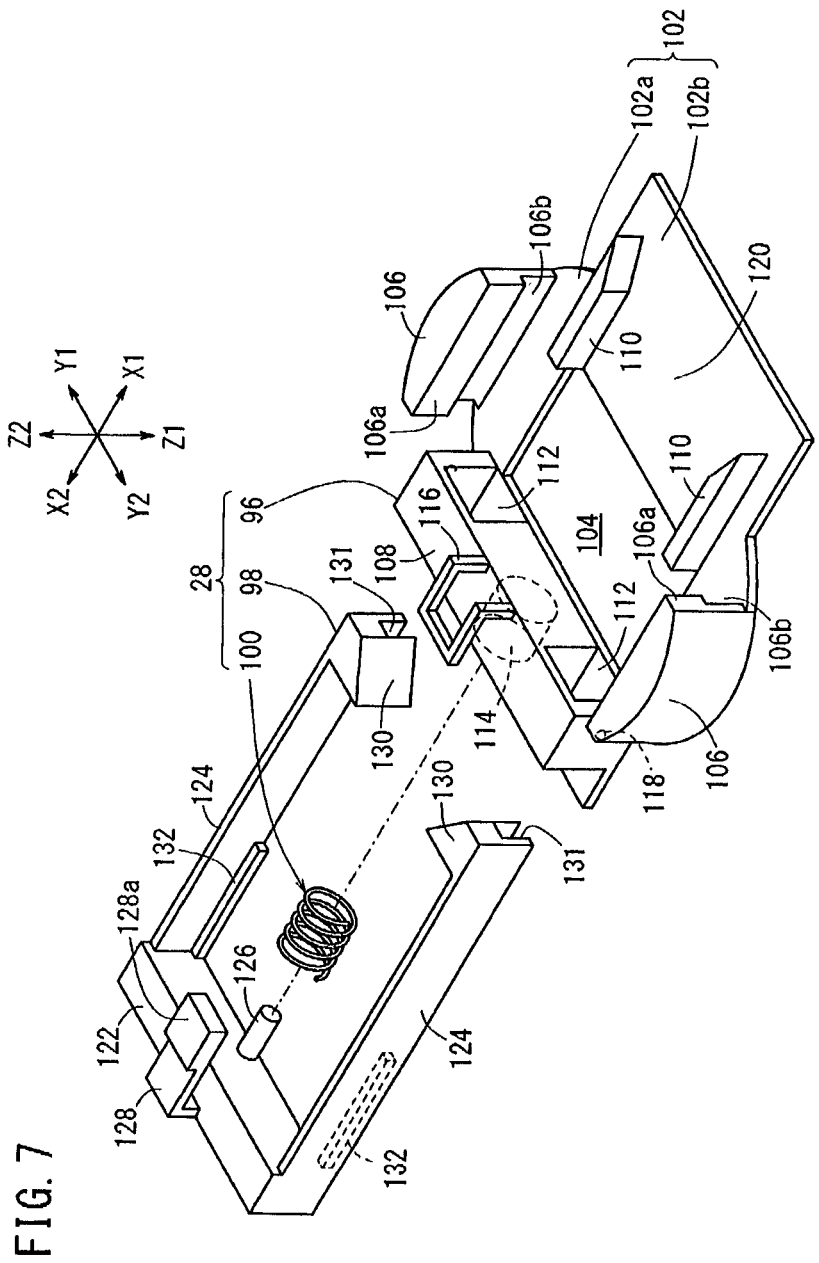
FIG. 7 is a perspective view in which the slider mechanism in FIG. 3 is enlarged.

As illustrated in FIG. 3 and FIG. 7, the slider mechanism 28 of the device body 18 is a mechanism in which, before an inserting operation of the sensor 12 (sensor unit 50) and the insertion needle 32, the dwelling member 24 is supported just below the housing 26 (distal end portion) and at the same time the transmitter 16 is supported in front (in the X1 direction) of the dwelling member 24, and after the inserting operation, the transmitter 16 is allowed to slide toward the dwelling member 24.

The slider mechanism 28 includes a slider mechanism body 96 which is attached to the housing 26, a slider 98 which is allowed to move relative to the slider mechanism body 96, and a slider spring 100 which gives thrust to (presses) the slider 98 toward the X2 direction.

The slider mechanism body 96 includes, in the distal end (Z1 direction) side, a body base 102 possessing a plate-like shape. The body base 102 is configured with a rear floor 102a having an approximately elliptical shape in a plan view and a rectangular front floor 102b continuously connected to the side, in the minor axis direction (the forward side), of the elliptical shape. The top surface of the body base 102 in which the rear floor 102a and the front floor 102b are continuously connected is provided as a transmitter arrangement portion 120. Further, in the approximately middle portion of the rear floor 102a, a rectangular dwelling member window 104 is drilled so as to have a size approximately the same as the plane shape of the dwelling member 24. The dwelling member 24 is previously arranged in the dwelling member window 104. Further, on the top surface of the body base 102, a pair of side walls 106, a rear wall 108, and a pair of slider guides 110 are arranged.

The pair of side walls 106 is vertically provided at both ends, in the major axial direction (Y direction), of the rear floor 102a, and extends in the front-and-rear direction (X direction) approximately parallel to each other. A brim 106a protruding inward is provided on an upper end portion of each side wall 106, and a gap 106b is formed between the brim 106a and the body base 102. When the housing 26 is attached to the slider mechanism body 96, the engaging plate 92c (see FIG. 6A) of the attachment arm 92 is inserted or positioned in the gap 106b.

The rear wall 108 is located in the rear of, and between, the pair of side walls 106 and provided to extend in the direction perpendicular to the direction toward which the side wall 106 extends. A slider inserting hole 112 penetrating the rear wall 108 in the front-and-rear direction is provided on each side, in the width direction (Y direction), of the rear wall 108. Further, a spring arrangement hole 114 in which the slider spring 100 is positioned is extends into and opens to the rear surface side, in the middle portion in the width direction, of the rear wall 108.

Further, on the top surface, and in the middle portion in the width direction, of the rear wall 108 (above the spring arrangement hole 114), a slider engaging portion 116 is formed. The slider engaging portion 116 is configured with a rectangular bar having a predetermined thickness. The slider engaging portion 116 extends upward from the top surface of the rear wall 108, and then, at a predetermined height, extends rearward to form a U-shape in a plan view. The slider engaging portion 116 functions as an engaging mechanism which restricts sliding of the slider 98.

Furthermore, a slider mechanism side protrusion 118 is protrudingly formed on the side surface, in the width direction, of the rear wall 108. The slider mechanism side protrusion 118 engages with the housing side recess 94 (see FIG. 6B) when the housing 26 and the slider mechanism body 96 are attached, thereby further strengthening the attachment.

The pair of slider guides 110 extend parallel to each other between the pair of side walls 106 and in front of the dwelling member window 104. A transmitter arrangement portion 120 is formed between the pair of slider guides 110.

Further, a slider 98 of the slider mechanism 28 is attached in a manner that the slider 98 is allowed to slide in the front-and-rear direction (X direction) against or relative to the slider mechanism body 96. The sliding operation of the slider 98 is carried out to move the transmitter 16 which is arranged in the transmitter arrangement portion 120 to be connected (integrated) with the dwelling member 24 which is previously arranged in the dwelling member window 104 (also see FIG. 19A to FIG. 19C).

The slider 98 possesses an approximate U-shape in a plan view and is attached to the slider mechanism body 96 so as to surround the rear wall 108 and the slider guide 110 of the slider mechanism 28 described above. The slider 98 includes a slider side connecting portion 122 extending toward the right-and-left width direction (Y direction), a pair of support arms 124 extending forward from both the right-and-left ends of the slider side connecting portion 122, a slider spring supporting protrusion 126 which supports the slider spring 100, and a slider controlling plate 128 which controls a timing of the movement of the slider 98.

The slider side connecting portion 122 has a width in the longitudinal direction (Y direction) corresponding to the length between the pair of slider inserting holes 112 of the slider mechanism body 96, and bridges the pair of support arms 124 located at both ends. In the middle portion in the width direction of the slider side connecting portion 122, the slider spring supporting protrusion 126 and the slider controlling plate 128 are provided.

The pair of support arms 124 are each a plate-shaped member and extend parallel to each other and toward the forward direction (X1 direction) from the slider side connecting portion 122. A slider side hook 130 is provided on the forward end of each of the pair of support arms 124. Each slider side hook 130 protrudes inward from the inner surface of the support arm 124 and is formed so as that the rear end surface of the protrusion is perpendicular to the support arm 124. Further, only the upper side of the slider side hook 130 is connected to the inner surface of the support arm 124. The lower side of the slider side hook 130 is provided with a hollow (groove) 131 in which the slider guide 110 can be inserted.

Further, on the portion of the inner surface of each of the pair of support arms 124 close to the slider side connecting portion 122, a rib 132 extends in the lengthwise direction of the support arm 124. The ribs 132 support the dwelling member 24 with the dwelling member 24 arranged in the dwelling member window 104 before the inserting operation of the sensor 12 and the insertion needle 32. The ribs 132 are connected to the slider side connecting portion 122 so as to suppress the swinging of the support arm 124, which also functions as a stiffening member for keeping the parallel state.

Further, the slider spring supporting protrusion 126 is a column-shape component protruding forward from the front surface of the slider side connecting portion 122 and facing the spring arrangement hole 114 when the slider 98 is assembled to the slider mechanism body 96.

Further, the slider controlling plate 128 extends forward by a predetermined height from the top surface of the slider side connecting portion 122, and is flexibly deformable in the up-and-down direction. On the forward portion of the slider controlling plate 128, a stepped portion 128a having a greater thickness than the rear portion is formed. The stepped portion 128a can engage with the slider engaging portion 116 (rectangular bar) of the slider mechanism body 96.

In the slider mechanism 28, the slider side connecting portion 122 is arranged in the rear of the rear wall 108 with the slider 98 and the slider spring 100 assembled in the slider mechanism body 96. Further, the pair of support arms 124 extends forward through the slider inserting holes 112, further advancing over the pair of slider guides 110, and reaching the front end portion of the front floor 102b of the body base 102.

Further, one end of the slider spring 100 is inserted in the spring arrangement hole 114 of the slider mechanism body 96, and the other end of the slider spring 100 is engaged with the slider spring supporting protrusion 126 of the slider 98.

Further, the slider controlling plate 128 of the slider 98 engages with the slider engaging portion 116 of the slider mechanism body 96. That is, the movement (sliding) of the slider 98 is restricted by the stepped portion 128a hooked in the rectangular bar of the slider engaging portion 116. When the sliding is restricted, the slider spring 100 is arranged in a compressed state. Therefore, in this state, the slider spring 100 gives thrust to the slider side connecting portion 122 of the slider 98 to move farther from the rear wall 108 (rearward).

In the manner described above, the slider mechanism 28 causes the slider 98 to slide rearward at a predetermined timing by assembling the slider mechanism body 96, the slider 98, and the slider spring 100. Further, in the slider mechanism body 96, when assembling the slider 98, the dwelling member 24 is assembled so as to overlap with or overlie the dwelling member window 104.

In the device body 18, the slider mechanism 28 to which each of the members is assembled as described above is attached to the distal end attachment portion 84 of the housing 26 (also see FIG. 6A and FIG. 6B). In this case, the slider mechanism body 96 is inserted in the pair of attachment arms 92 from the front side. Specifically, the engaging plate 92c of the attachment arm 92 is engaged with the brim 106a of the side wall 106 and the gap 106b of the body base 102, and then the slider mechanism body 96 is inserted rearward. In this manner, the attachment arm 92 is held between the side surface of the rear wall 108 and the side surface of the side wall 106. In this state, by inserting (sliding) the slider mechanism 28, the slider mechanism 28 is attached to the housing 26. At this time, when the insertion is carried out until the rear end surface of the side wall 106 of the slider mechanism 28 makes contact with the longitudinal plate 92d of the attachment arm 92, the slider mechanism side protrusion 118 of the slider mechanism body 96 engages with the housing side recess 94. In this manner, disengagement of the slider mechanism 28 from the housing 26 can be prevented.

Referring again to FIG. 3, the movement mechanism 20 provided in the device body 18 includes the head 30, the advance spring 34, and the return spring 36. The head 30 is arranged so as to be movable in the up-and-down direction in the device body 18 (housing 26).

Figure 8A:
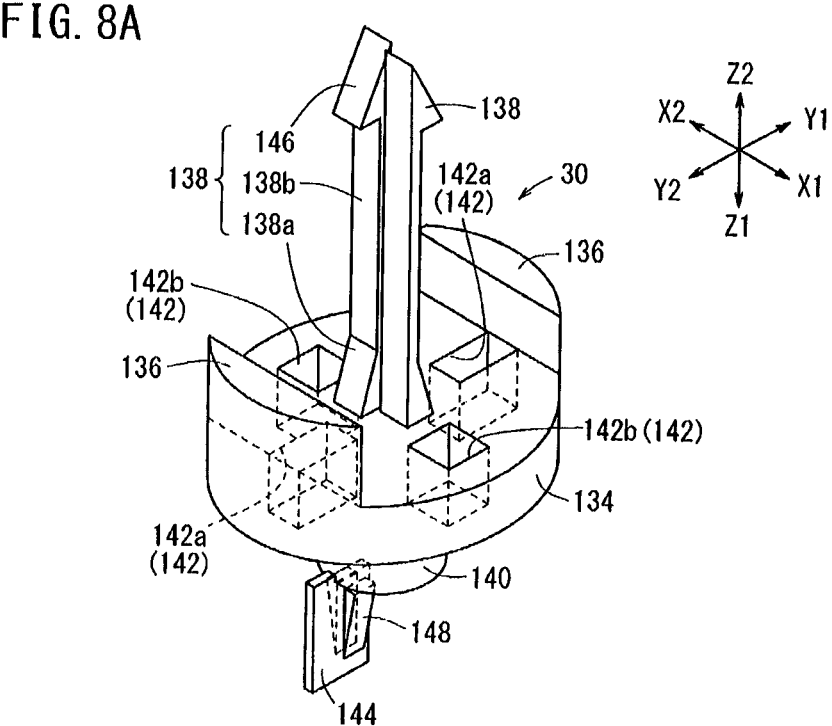
FIG. 8A is a perspective view of the head in FIG. 3
Figure 8B:
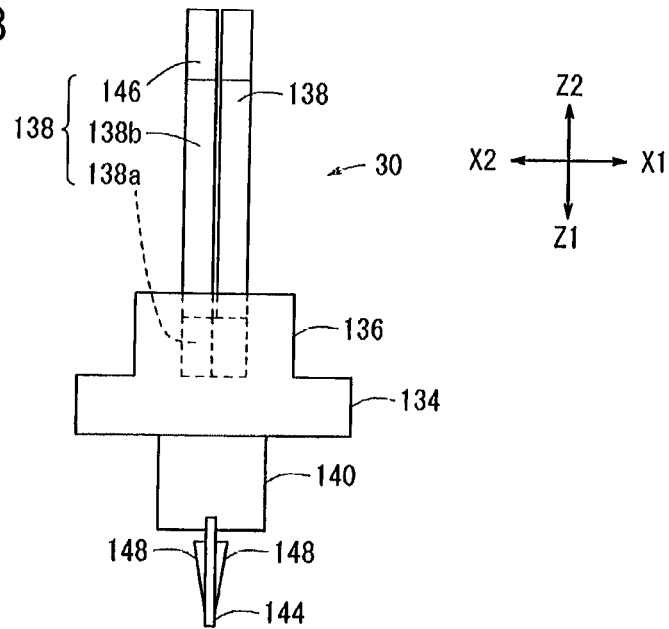
FIG. 8B is a side view of the head in FIG. 3.
Figure 11C:
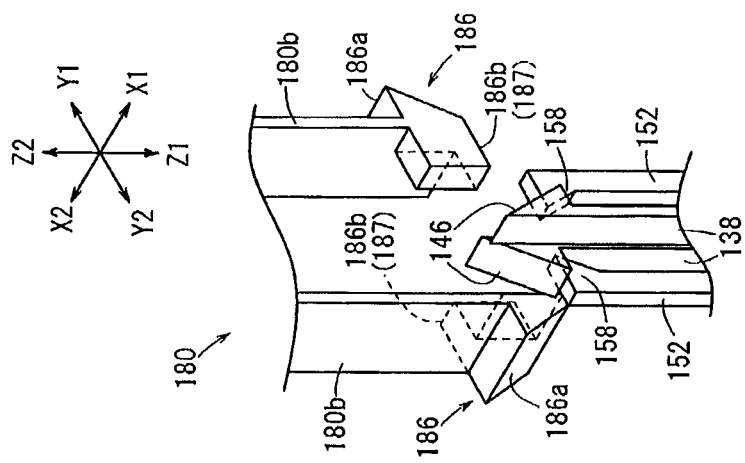
FIG. 11C is an essential perspective view in which an operating bar of the push handle in FIG. 3 is enlarged.
Figure 11B:
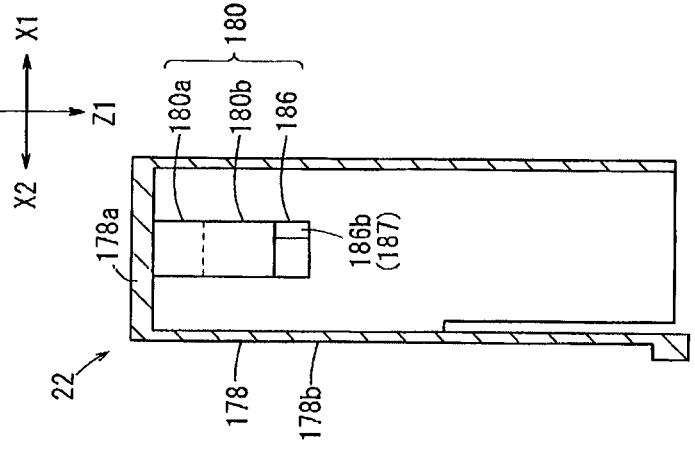
FIG. 11B is a cross-sectional view taken along the section line XIB-XIB in FIG. 11A.
Figure 11A:
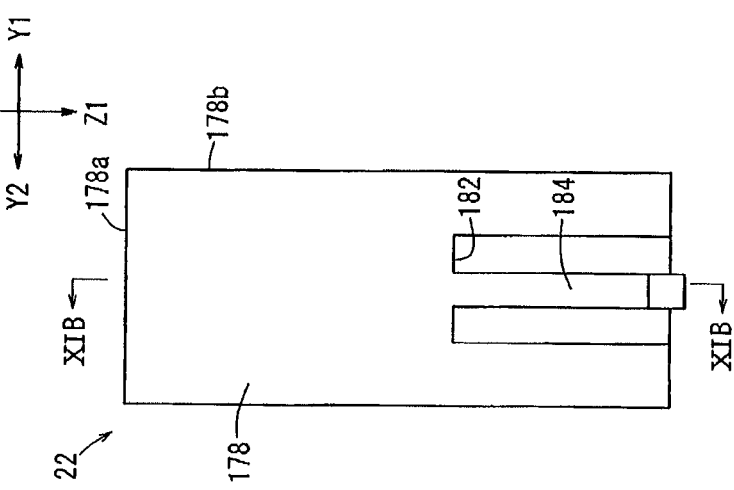
FIG. 11A is a rear view of the push handle in FIG. 3.

As shown in FIG. 8A and 8B, the head 30 includes an elliptical plate (head base) 134 having an elliptical shape in a plan view, head side guides 136 formed on both ends of the major axial direction (Y direction) of the elliptical plate 134, a pair of head side arms 138 extending upward (Z2 direction) from the top surface of the elliptical plate 134, a lower side protrusion 140 protruding downward (Z1 direction) from the bottom surface of the elliptical plate 134, a plurality of head side inserting holes 142 penetrating the elliptical plate 134, and head side support plates 144 protruding further downward from the bottom of the lower side protrusion 140. The head 30 is arranged between the pair of extending portions 82 (see FIG. 4) so as to slide in the up-and-down direction.

The elliptical plate 134 is a base having the head side guide 136, the head side arm 138, and the lower side protrusion 140 on the surface. The elliptical plate 134 is configured as a component which receives the thrust (pressing force) from the advance spring 34 and the return spring 36 which are force producing sources of the movement mechanism 20. The elliptical plate 134 can be formed of the same material as the housing 26, and is formed so as to have the dimension in the major axial direction approximately same as the inner diameter of the pair of extending portions 82 and a predetermined thickness. In this manner, the elliptical plate 134 is provided with sufficient rigidity so that the shape of the elliptical plate 134 can be retained even when the thrust from the advance spring 34 and the return spring 36 is applied.

The pair of head side guides 136 formed on both ends of the elliptical plate 134 extends upward (Z2 direction) from the top surface of the elliptical plate 134. The outer surface of the head side guide 136 is an arc-shape which is approximately the same as the inner surface of the extending portion 82. That is, by the outer surface of the pair of head side guides 136 sliding against the inner surface of the extending portion 82, movements in the front-and-rear and right-and-left directions and the rotation of the head 30 are restricted so that the head 30 is guided to move only in the up-and-down direction.

The pair of head side arms 138 is provided in the approximately middle (axial center) of the elliptical plate 134, and extends upward via the lower side connecting portion 138a continuously connected to the elliptical plate 134 and a plate-like extending portion 138b constituting the middle portion. A head side hook 146 is formed on the upper end portion of the head side arm 138. The head 30 is supported at approximately the middle portion of the housing 26 by the head side hook 146 engaging with the fixing member 38 (see FIG. 4). Further, the pair of head side arms 138 is arranged so as that the pair of head side arms 138 is adjacent to each other in the front-and-rear direction (X direction) in a side view (see FIG. 8B) and the plate-shaped extending portions 138b overlap each other in a front view. Further, the lower side connecting portion 138a has a tapered shape in which the width is larger in the portion connected to the elliptical plate 134 and becomes smaller toward an upper portion. Thereby, the lower side connecting portion 138a is stiffened so that the swinging of the tapered surface side of the head side hook 146 is restrained. Furthermore, each of the pair of head side hooks 146 has a hooking portion protruding in the same direction as the tapered shape of the lower side connecting portion 138a. In the front view, the hooking portions protrude toward the opposite side to each other. That is, when the head side arm 138 engages with the fixing member 38, the central axis of the head 30 is firmly supported, and thereby the disengagement of the head side hook 146 caused by an effect other than a predetermined operation (e.g., vibration of the sensor inserting device 10 or an impact of external force) can be prevented.

Further, the lower side protrusion 140 is formed on the column-like portion protruding by a predetermined distance from the middle portion of the bottom surface of the elliptical plate 134.

Further, the head side inserting holes 142 provided on the elliptical plate 134 are drilled or located at four (front, rear, right, and left) locations surrounding the head side arm 138. The four head side inserting holes 142, at locations facing each other with the head side arm 138 in between, have the same shape. Specifically, a pair of first head side inserting holes 142a located on the major axial direction of the elliptical plate 134 each possess an approximately rectangular shape, and second head side inserting holes 142b located on the minor axial direction each possess an approximately square shape. First and a second guide arms 166 and 168 of the guiding member 40 (see FIG. 3) are inserted in each pair of head side inserting holes 142a and 142b.

The head side support plate 144 has a function to attach and support the insertion needle 32, and is provided in the left (Y2 direction) side, in a front view, of the bottom of the lower side protrusion 140. The head side support plate 144 is plate-shaped and protrudes downward (distal end direction). Further, on both sides of the plate of the head side support plate 144, an engagement protrusion 148 formed in a tapered shape having a smaller thickness toward the lower portion is provided. The engagement protrusion 148 possesses a rectangular shape which is approximately the same as the shape, in a front view, of the insertion needle side attaching hole 78 (see FIG. 5) of the insertion needle 32. The insertion needle side attaching hole 78 engages with or is positioned in the engagement protrusion 148. That is, when the insertion needle 32 is attached to the head 30, the head side support plate 144 is sandwiched between the two airfoil portions 74 of the insertion needle 32 and the engagement protrusion 148 is inserted into the insertion needle side attaching hole 78. In this manner, the insertion needle 32 is firmly supported by the head 30.

Referring again to FIG. 4, in the movement mechanism 20 according to the embodiment disclosed by way of example, regarding the head 30, the advance spring 34 is arranged in the upper side of the elliptical plate 134 and the return spring 36 is arranged in the lower side of the elliptical plate 134. In this case, the elastic force of the advance spring 34 is larger than the elastic force of the return spring 36.

The advance spring 34 is arranged to surround the pair of head side arms 138 between the elliptical plate 134 of the head 30 and the fixing member 38. The advance spring 34 is shorter than the head side arm 138. However, when the head 30 is engaged with the fixing member 38 (before inserting operation of the sensor unit 50 and the insertion needle 32), the advance spring 34 is compressed in the axial direction so as to give downward thrust to the elliptical plate 134 (that is, head 30). Therefore, the advance spring 34 functions as a force producing source for moving the head 30 toward the distal end direction before the inserting operation, and provides a piercing force to insert (make piercing with) the sensor unit 50 and the insertion needle 32 into the body of the patient at the distal end of the device body 18.

Further, the return spring 36 is arranged to surround the periphery of the guiding member 40 on the top surface of the distal end attachment portion 84 of the housing 26. In this case, the return spring 36 is not in contact with the head 30 before the inserting operation of the sensor unit 50 and the insertion needle 32. Further, when the head 30 moves toward the distal end direction as the inserting operation proceeds, the return spring 36 is compressed and produces thrust to push the head 30 back toward the proximal end direction.

In this manner, in the movement mechanism 20, the head 30 is supported at an approximately middle location in the housing 26 (standby position) by the fixing member 38 before the inserting operation of the sensor unit 50 and the insertion needle 32. When the supported state is cancelled by a predetermined operation, the movement toward the distal end direction guided along the guiding member 40 is produced.

The fixing member 38 is arranged in the gap 90a (see FIG. 6A) between the proximal end cylindrical portion 80 and the proximal end side protruding portion 90 of the housing 26, and has a function of supporting the head 30 before the inserting operation of the sensor unit 50 and the insertion needle 32 as described above. As illustrated in FIG. 9A to FIG. 9C, the fixing member 38 includes a middle disk (fixing base) 150 provided in an approximately middle portion in the up-and-down direction, a pair of fixing member side arms 152 extending upward from the top surface of the middle disk 150, and a pair of guiding feet 154 extending downward from the bottom surface of the middle disk 150.

The middle disk 150 is configured as a component receiving the thrust (pressing force) from the advance spring 34 and formed in a disk-like shape of which outer diameter and thickness are approximately the same as those of the gap 90a of the housing 26. Therefore, the fixing member 38 is inserted in the gap 90a, and thereby firmly fixed and supported in the housing 26. Further, in the approximately middle portion of the middle disk 150, a rectangular fixing member side inserting hole 156 is drilled located. In the fixing member side inserting hole 156, the pair of head side arms 138 (see FIG. 8A) is inserted.

The pair of fixing member side arms 152 is formed at sides of the fixing member side inserting hole 156, in the right-and-left width direction (Y direction), in a plate-like shape with a smaller thickness in the front-and-rear direction and extends upward by a predetermined distance. On the upper portion of the fixing member side arm 152, a supporting protrusion 158 with which the head side hook 146 of the head side arm 138 engages is inwardly formed. The pair of the fixing member side arms 152 is arranged to be offset to each other in the front-and-rear direction, in a side view, corresponding to the arrangement of the head side arm 138. Further, the supporting protrusion 158 is formed in a tapered shape in which the width increases inward from a predetermined location close to the upper portion so that tilting toward the inner side is restrained, thereby providing further firm engagement of the head side hook 146.

The pair of guiding feet 154 is connected to the bottom surface of the middle disk 150 and extend downward by a predetermined distance. The pair of guiding feet 154 is formed in a location displaced in a circumferential direction of the middle disk 150 by 90 degrees from the fixing member side arm 152. Further, as illustrated in FIG. 9C, a fixing member side groove 160 is located on the outer side in the width direction and along the extending direction of the guiding foot 154. A fixing member side hook 162 protruding outward is provided in the lower side of the fixing member side groove 160. The fixing member side hook 162 engages with the second guide arm 168 of the guiding member 40.

As illustrated in FIG. 10A to FIG. 10C, the guiding member 40 has a function of guiding the movement of the head 30 toward the distal end direction during the inserting operation of the sensor unit 50 and the insertion needle 32, and is configured to move toward the proximal end direction with the head 30 after the inserting operation of the sensor unit 50 and the insertion needle 32. To provide such operation, the guiding member 40 is configured to include a ring portion 164 formed in the lower side, the pair of first guide arms 166 extending upward from both ends in the right-and-left width direction (Y direction) of the ring portion 164, and the pair of second guide arms 168 extending upward from both ends in the front-and-rear direction (X direction) of the ring portion 164.

The ring portion 164 is ring-shaped having a predetermined thickness, and vertically supports the first and second guide arms 166 and 168. Before the inserting operation of the sensor unit 50 and the insertion needle 32, the ring portion 164 is arranged inside the distal end portion (pair of attachment arms 92) of the housing 26 (see FIG. 4). Further, as illustrated in FIG. 10C, the inner circumference surface of the ring portion 164 in the vicinity of the first guide arm 166 includes an upright groove 170 which engages with the engaging arm 44 to support the upright position.

The pair of first guide arms 166 is formed to have a cross-section, which allows the first guide arm 166 to be inserted in the first head side inserting hole 142a (see FIG. 8A) of the head 30, and extends upward by a predetermined distance. Further, the upper end of the first guide arm 166 is notched so as to form a tapered shape on the outer side in the width direction. Further, the first guide arm 166 has a swingably engaging plate 172 which is swingable, along the notched surface, in the width direction.

One end of the swingably engaging plate 172 is connected to the upper end of the first guide arm 166, and the other end of the swingably engaging plate 172 can swing about the connecting portion. That is, before the inserting operation of the sensor unit 50 and the insertion needle 32, the swingably engaging plate 172 spreads out in the width direction so that the other end makes contact with the inner surface of the extending portion 82. Then, by the inserting operation (movement of the head 30 toward the distal end direction), the swingably engaging plate 172 swings toward the closing direction (direction toward the first guide arm 166) by making contact with the head side inserting hole 142, thereby allowing the head 30 to pass. Further, when the head 30 moves toward the proximal end direction, the other end of the swingably engaging plate 172 makes contact with the head side guide 136, thereby transmitting the force of motion toward the proximal end direction from the head 30 to the guiding member 40, so that the guiding member 40 moves toward the proximal end direction with the head 30.

Furthermore, each inner side of the pair of first guide arms 166 includes an arm groove 174 which extends from the upper portion of the first guide arm 166 to the lower end of the ring portion 164 continuously connected to the first guide arm 166. In one of the pair of arm grooves 174, a sensor side guiding portion 62 of the sensor unit 50 (see FIG. 5) is inserted, and in the other arm groove 174 in the opposite side, a head side support plate 144 of the head 30 is inserted. That is, the guiding member 40 can guide the sensor unit 50 and the insertion needle 32 toward the distal end direction by the arm groove 174 when the head 30 moves. In the approximately middle portion of the arm groove 174, a temporary-engaging protrusion 174a slightly protrudes inward. The temporary-engaging protrusion 174a makes contact with the distal end portion of the sensor side guiding portion 62 of the sensor unit 50 before the inserting operation of the sensor unit 50 and the insertion needle 32 so that disengagement of the temporarily held sensor unit 50 from the insertion needle 32 can be prevented.

The pair of second guide arms 168 is formed to have a cross section which allows the insertion in the second head side inserting hole 142b of the head 30. Each second guide arm 168 extends by a length approximately the same as that of the pair of first guide arms 166 and has, on the upper end, a guiding member side hook 176 protruding inward. The second guide arms 168 enter the respective fixing member side groove 160 formed on the guiding foot 154 of the fixing member 38 so that the guiding member side hook 176 engages with the fixing member side hook 162. Thereby, the guiding member 40 is supported by the fixing member 38, but the movement toward the distal end direction is restricted. Further, when the guiding member 40 moves toward the proximal end direction, the fixing member side groove 160 guides the second guide arm 168 (guiding member side hook 176).

Referring again to FIG. 2 and FIG. 4, a push handle 22 is attached to the proximal end (Z2 direction) side of the device body 18 (housing 26) of the sensor inserting device 10. The push handle 22 has a function of releasing the engagement of the head 30 supported by (engaged with) the fixing member 38 when the inserting operation of the sensor unit 50 and the insertion needle 32 is carried out. The push handle 22 is attached so as to be allowed to move toward the distal end direction (Z1 direction) relative to the device body 18. This displacement releases the engagement of the head 30. That is, in the movement mechanism 20, the movement of the head 30 toward the distal end direction (inserting operation) is carried out by the operation of the push handle 22.

As illustrated in FIG. 3 and FIG. 11A to FIG. 11C, the push handle 22 according to the illustrated embodiment disclosed by way of example includes an outer cylinder 178, possessing a bottomed cylindrical shape and covering the upper portion of the device body 18 (housing 26), and the pair of operating bars 180 provided inside the outer cylinder 178.

The outer cylinder 178 is attached so as to cover the upper portion (proximal end side) of the device body 18. The upper bottom portion 178a of the outer cylinder 178 possesses, in a plan view, an elliptical shape whose area is somewhat larger than that of the proximal end cylindrical portion 80 of the housing 26. A side circumferential portion 178b continuously connected to the periphery of the upper bottom portion 178a surrounds the proximal end cylindrical portion 80 and a portion of the extending portion 82 and extends toward the distal end (Z1 direction). Further, a notch 182 is formed in the rear surface (X2 direction) side of the side circumferential portion 178b, close to the distal end portion, of the outer cylinder 178. Further, a push handle side pressing plate 184 extending toward the distal end direction is provided on the top side of the notch 182. The push handle side pressing plate 184 is formed in a shape which allows the distal end portion of the push handle side pressing plate 184 to be inserted in the slider engaging portion 116 of the slider mechanism 28. The push handle side pressing plate 184 extends somewhat longer than the distal end of the side circumferential portion 178b. When the push handle 22 is attached to the device body 18, the distal end portion and the slider controlling plate 128 of the slider mechanism 28 face each other.

Further, the pair of operating bars 180 hangs toward the distal end side from the bottom surface of the upper bottom portion 178a. The operating bar 180 includes an operating bar side connecting portion 180a which is connected to the outer cylinder 178 at the upper side, a middle swinging portion 180b which extends toward the distal end from the operating bar side connecting portion 180a, and an operating bar side hook 186 formed on the distal end portion. The operating bar side connecting portion 180a possesses a tapered shape, in which the width is larger at the proximal end side and becomes smaller toward the distal end side, and firmly supports the middle swinging portion 180b and the operating bar side hook 186. In the illustrated embodiment, the operating bar side connecting portion 180a, the middle swinging portion 180b, and the operating bar side hook 186 of each operating bar 180 are integrally formed in one piece at the same time as a single unit. The middle swinging portion 180b is formed in a thin plate-shape and continuously connected to the operating bar side connecting portion 180a so that the operating bar side hook 186 on the distal end portion can swing in the thickness direction.

The pair of the operating bar side hooks 186 includes a hooking portion 186a protruding outward in the width direction and a contact portion 186b protruding inward in the width direction from the opposite side of the hooking portion 186a. The pair of the hooking portions 186a is formed in a shape which allows engagement with the plurality of teeth 88 surrounding the internal space 86 of the housing 26 (a right triangular shape having an inclined surface and an engaging surface). Further, the pair of contact portions 186b is formed in a rectangular protruding piece 187 having a thickness smaller than the thickness in the front-and-rear direction of the hooking portion 186a. The pair of the contact portions 186b is provided in locations so as not to overlap with each other in the front-and-rear direction (X direction). Specifically, for the operating bar 180 in the left side in a front view, the protruding piece 187 is positioned close to the rear side of the hooking portion 186a, and for the operating bar 180 in the right side, the protruding piece 187 is positioned close to the front side of the hooking portion 186a.

As illustrated in FIG. 4, by attaching the push handle 22 to the housing 26 so as to cover the housing 26 from above, the operating bar 180 is inserted toward the internal space 86 through the top surface opening. In this process, as for the operating bar 180 of the push handle 22, the operating bar side hook 186 is guided along the top surface opening, and the hooking portion 186a engages with the upper bottom portion 80a (wall surface) of the housing 26. In this state, the inclined surface of the hooking portion 186a of the operating bar side hook 186 makes contact with the inclined surface of the first tooth 88a, thereby restraining looseness of the operating bar 180 (that is, the push handle 22). By the engagement of the operating bar 180, the disengagement of the push handle 22 from the housing 26 is prevented.

Further, when the inserting operation of the sensor unit 50 and the insertion needle 32 is carried out, by displacing the push handle 22 toward the distal end direction of the device body 18 (that is, pushing the push handle 22 toward the distal end direction), the operating bar 180 is displaced simultaneously. When the displacement is carried out, the operating bar side hook 186 deflects inward so as to go over the first tooth 88a. By virtue of this inward deflection, the contact portion 186b of the operating bar 180 contacts the head side arm 138 (head side hook 146). As for the contact portion 186b, since each of the pair of protruding pieces 187 is provided in a location offset from each other in the front-and-rear direction as described above, each protruding piece 187 has an offset in the front-and-rear direction between the arrangement of the fixing member side arm 152 of the fixing member 38 (see FIG. 11C). Therefore, even when the protruding piece 187 deflects inward, the collision against the fixing member side arm 152 of the fixing member 38 is avoided. That is, the protruding piece 187 only makes contact with the head side hook 146 so as to release the engagement of the head side hook 146 from the fixing member side arm 152. In this manner, the head 30 is separated from the fixing member 38.

Now, the dwelling member 24 which allows the sensor unit 50 to dwell on the skin S of the patient and the transmitter 16 which is connected to the sensor unit 50 will specifically be described. As described above, the dwelling member 24 is a member which supports and allows the sensor unit 50 and the transmitter 16 to dwell on the skin S of the patient. The dwelling member 24 includes the base 42 arranged in the slider mechanism 28, the engaging arm 44 rotatably supported by the base 42, and the adhesive sheet 46 (see FIG. 3) which sticks on the skin S of the patient and allows the base 42 to dwell on the skin S of the patient.

Figure 12A:
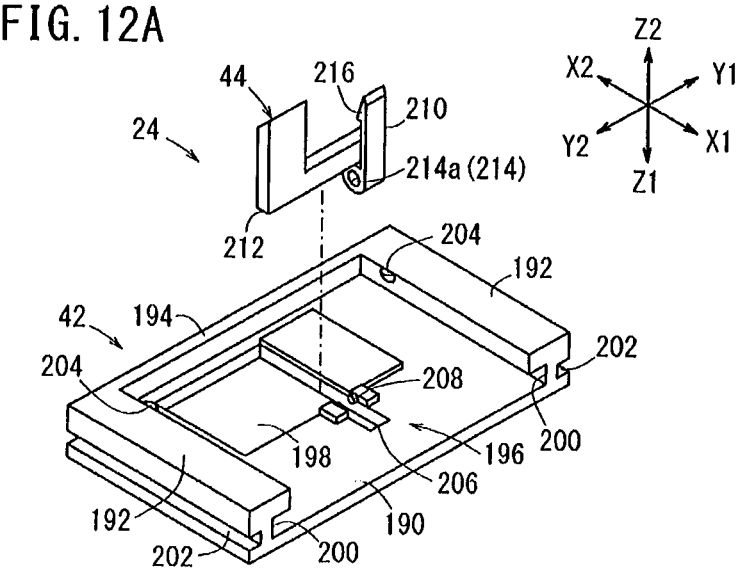
FIG. 12A is an exploded perspective view in which the dwelling member in FIG. 3 is enlarged and FIG. 12B is a perspective view in which the assembled dwelling member is enlarged.
Figure 12B:
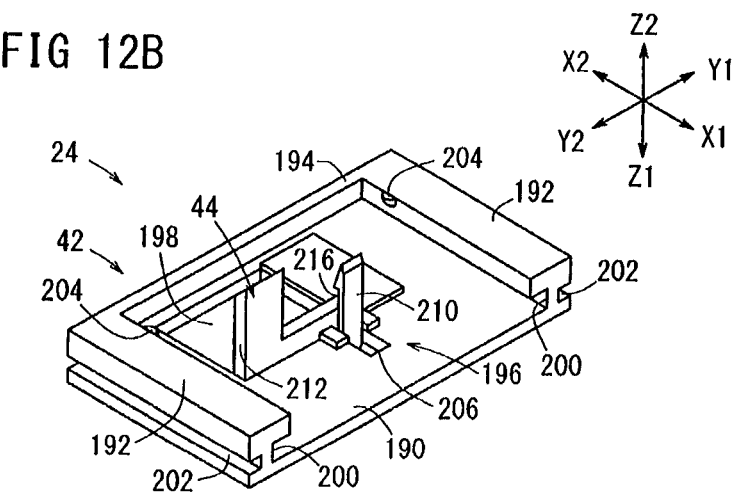

As illustrated in FIG. 12A and FIG. 12B, the base 42 is formed in a shape which allows the transmitter 16 to be inserted from the front side. That is, by the sliding operation of the transmitter 16 provided by the slider mechanism 28, the transmitter 16 is inserted in the base 42. The base 42 includes a floor 190 formed in a rectangular shape in a plan view located on a bottom side, a pair of side walls 192 vertically arranged on both ends of the floor 190 in the longitudinal direction (Y direction), a rear wall 194 which connects the pair of side walls 192, a base side pivot support 196 formed in an approximately middle portion of the floor 190, and a containing hole 198 drilled on and passing through the floor 190 adjacent to the base side pivot support 196.

The surface of the floor 190 surrounded by the side wall 192 and the rear wall 194 is configured to be an arrangement surface of the transmitter 16.

The pair of side walls 192 extends along the short direction of the floor 190 parallel to each other. A pair of supporting grooves 200 is formed on the inner side of the pair of side walls 192, and a pair of guiding grooves 202 is further formed on the sides, opposite to the pair of the supporting grooves 200, of the pair of the side walls 192 (outer side in the longitudinal direction of the floor 190). Further, in the inner surface of the side wall 192 close to the rear side, a base side protrusion 204 protruding inward is provided.

The supporting groove 200 is formed to have a width in which a side protrusion 218 of the transmitter 16 (see FIG. 3), which will be described below, can be inserted. That is, when the transmitter 16 is slidably inserted in the base 42, the supporting groove 200 and the side protrusion 218 engage each other so that the transmitter 16 is supported in the base 42 (dwelling member 24). Further, the guiding grooves 202 possess a width allowing the ribs 132 (see FIG. 7) of the slider 98 to be inserted into the guiding grooves 202. When the base 42 is arranged in the slider mechanism 28, the inner wall surface forming the dwelling member window 104 restricts movements of the base 42 in the front-and-rear and right-and-left directions. And the rib 132 restricts the movement of the base 42 in the up-and-down direction so that the dwelling member 24 is supported in the slider mechanism 28 (see FIG. 3). Further, during the sliding operation of the slider 98, the slider 98 is guided by the guiding groove 202.

As illustrated in FIG. 12A, the rear wall 194 connecting the side walls 192 determines the slide limit of the transmitter 16.

The base side pivot support 196 is a component which pivotally supports engaging arm 44 and includes a notched groove 206 formed on the floor 190 so as to continuously connect the containing hole 198 and a pair of opposingly positioned pivotally supporting protrusions 208. The protrusions are disposed at locations along opposite sides of the notched groove 206 so that the notched groove 206 is between the protrusions 208, and so that the protrusions 208 are slightly higher than the top surface of the floor 190. Each of the pivotally supporting protrusions 208 is positioned in the pivot hole 214a of the engaging arm 44 so as to pivotally support the engaging arm 44. Further, the notched groove 206 functions as a space for avoiding interference when the engaging arm 44 rotates.

The containing hole 198 is rectangular-shaped and is provided on the floor 190 at a position in a region spaced from an approximately middle portion toward the left side (Y2 direction). The plane shape of the containing hole 198 has dimensions larger than the width and height dimensions of the engaging arm 44 in a front view. That is, the containing hole 198 can contain or receive the engaging arm 44 when the engaging arm 44 turns and rotates down to be flat.

Further, the engaging arm 44 includes an extending engaging portion 210 formed in the Y1 direction and an L-shape portion 212 extending toward the Y2 direction from the side of the extending engaging portion 210.

The bearing 214 is provided on the lower (Z1 direction) side of the extending engaging portion 210. An engaging arm side hook 216 is formed on the upper portion extending from the bearing 214. The bearing 214 has a pivot hole 214a penetrating in the width direction and open at both ends. Each of the pivotally supporting protrusions 208 is positioned the pivot hole 214a when the engaging arm 44 is attached to the base 42. Further, the engaging arm side hook 216 is hooked on the hook 64a of the sensor side hook 64 (see FIG. 5) when the sensor unit 50 moves toward the distal end direction.

The L-shape portion 212 extends toward the Y2 direction by a length long enough to be inserted in the upright groove 170 on the inner surface of the ring portion 164 of the guiding member 40 (see FIG. 10C) and then, from the end portion, extends upward to form the shape (L-shape). The L-shape portion 212 is supported by the upright groove 170 in the inner side of the first guide arm 166. Thereby, the engaging arm 44 is supported to stand upright from the base 42 before the inserting operation of the sensor unit 50 and the insertion needle 32.

Referring again to FIG. 3, an adhesive having sufficient adhesion for sticking on the skin S of the patient without coming off easily is coated on the bottom surface (surface facing the distal end) side of the adhesive sheet 46. Further, the adhesive is also coated on the portion, directly facing the base 42, of the top surface (surface facing the proximal end) side of the adhesive sheet 46. Therefore, the dwelling member 24 with the adhesive sheet 46 adhered on the base 42 can be arranged in the slider mechanism 28 (see FIG. 1).

Figure 13A:
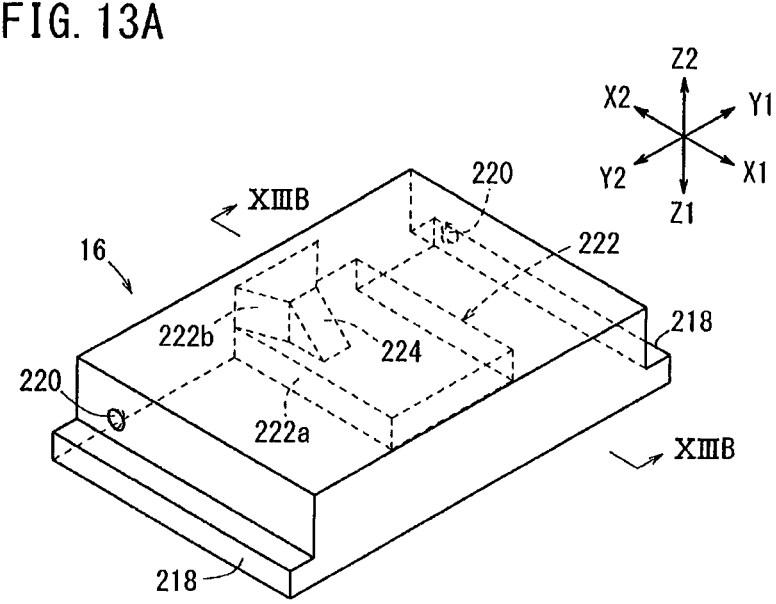
FIG. 13A is a perspective view in which the transmitter in FIG. 3 is enlarged and FIG. 13B is a cross-sectional view taken along the section line XIIIB-XIIIB in FIG. 13A.
Figure 13B:
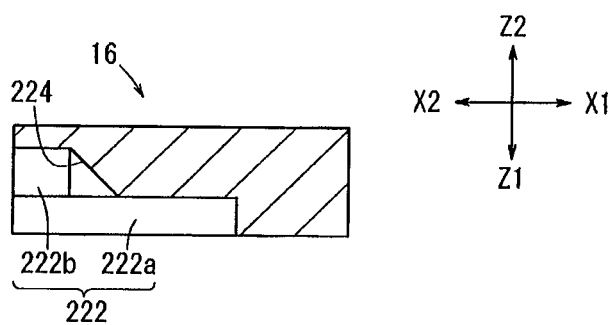

As illustrated in FIG. 13A, the transmitter 16 includes an approximately rectangular-shaped case which is inserted or positioned in, and supported by, the base 42. Inside the case of the transmitter 16, an electric (electronic) circuit structure which processes the blood sugar level (current value) detected by the sensor unit 50 (detector 14 of the sensor 12) illustrated in FIG. 5 is provided. In this case, the component of the electric circuit may be a current/voltage converter which converts a current value detected by the detector 14 of the sensor into a voltage value, an amplifier which amplifies a voltage value, a transmitter which externally transmits a voltage value (signal value) wirelessly (or wired), a battery which supplies power to each components, or a circuit substrate for electrically connecting components. Various configurations may be employed for the structure of the electric circuit and, for example, a microcomputer or the like which carries out a predetermined processing of a signal value may be implemented in the circuit substrate.

Both ends of the transmitter 16, in the longitudinal direction (Y direction) of the transmitter 16, are provided with a side protrusion 218 having a smaller thickness than the thickness of the main body. The protrusions 208 protrude outwardly or extend away from the main body. The side protrusions 218 engage with the supporting grooves 200 of the base 42 (see FIG. 12A) so that the transmitter 16 is supported by the base 42. Further, at a predetermined location on each side surface of the transmitter 16 close to the rear portion, a transmitter side recess 220 is formed. The transmitter side recesses 220 engage with the base side protrusion 204 of the base 42 when the transmitter 16 is slidably inserted so that the disengagement of the transmitter 16 from the base 42 can be prevented.

Further, a connecting terminal recess 222 is provided in the bottom surface of the transmitter 16 toward the rear portion of the transmitter 16. The sensor unit 50 (see FIG. 5)

is inserted in the connecting terminal recess 222. The connecting terminal recess 222 is located in the region from an approximately middle portion in the width direction, in a plan view, toward the right (Y1 direction) side. That is, the connecting terminal recess 222 is not centered in the bottom surface of the transmitter, but rather is located closer to one side, namely the right side in FIG. 13A. The connecting terminal recess 222 includes a first space 222a possessing a rectangular shape and opening to the bottom surface of the transmitter 16 and a second space 222b which is continuously connected to or in communication with the upper side of the first space 222a and has a relatively smaller area in a plan view. The first space 222a is configured to contain or receive the sensor 12 and the engaging member 52 of the sensor unit 50. The second space 222b is configured to contain or receive the connecting member 54. Note that, in the transmitter 16, the front portion side of the second space 222b is configured as a tapered surface 224 which is a conductive connecting surface configured to make electrical connection with the connecting member 54 (conductive terminal). Further, the second space 222b possesses a tapered shape expanding toward the rear side so that the connecting member 54 can be slidably inserted with ease.

The sensor inserting device 10 according to the embodiment is configured as described above. Now, the operation of insertion and dwelling of the sensor 12 using the sensor inserting device 10 will be described.

Figure 14:
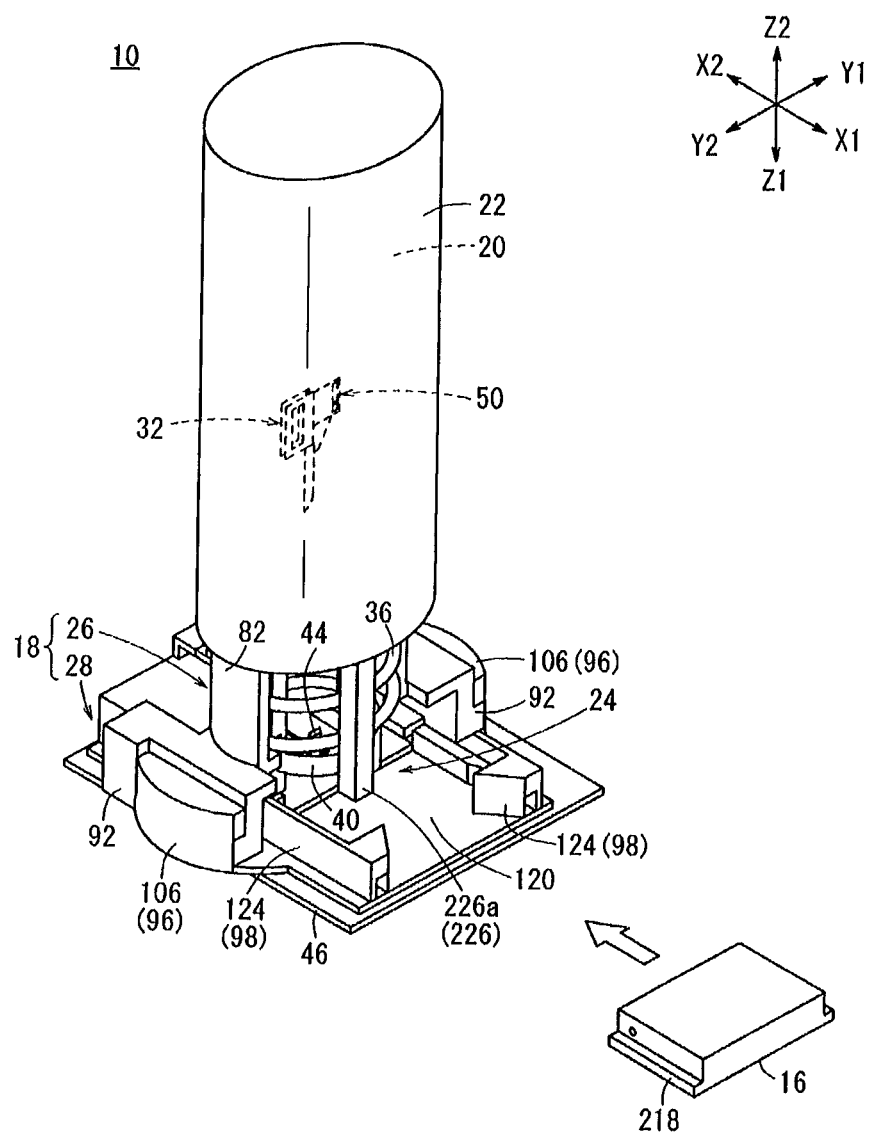
FIG. 14 is a perspective view illustrating a transmitter to be attached when using the sensor inserting device according to the embodiment.

FIG. 14 illustrates a transmitter 16 to be attached when using the sensor inserting device 10 according to the embodiment described above.

When the sensor inserting device 10 is used, the sensor unit 50 and the insertion needle 32 are previously attached to the movement mechanism 20 inside the device body 18, and the arrangement of the transmitter 16 to the sensor inserting device 10 in which the slider mechanism 28 and the dwelling member 24 is attached to the distal end portion of the device body 18 (the state the product is provided) is carried out.

In the state the product is provided, the safety mechanism 226 is provided to the sensor inserting device 10 so that the displacement (movement) of the push handle 22 toward the distal end direction (downward direction in FIG. 14) is restricted. The safety mechanism 226 according to the illustrated embodiment is configured as a fixing support bar 226a provided between the transmitter arrangement portion 120 of the slider mechanism 28 and the distal end of the push handle 22. The safety mechanism 226 restricts (prevents) the displacement or axial movement of the push handle 22 by virtue of the fixing support bar 226a supporting the push handle 22 on the transmitter arrangement portion 120, and further prevents arrangement of the transmitter 16. That is, in addition to preventing the axial movement of the push handle 22, the fixing support bar 226a prevents the transmitter from being moved into the position shown in FIG. 1. To attach or position the transmitter 16 at the position shown in FIG. 1, the fixing support bar 226a needs to be removed. In this manner, a trouble such as forgetting to release the safety mechanism 226 when the sensor inserting device 10 is to be used can be avoided.

After the transmitter 16 is attached to the sensor inserting device 10, the sensor inserting device 10 is positioned at a suitable location (location in which the sensor 12 is to be inserted) on the skin S of the patient as illustrated in FIG. 1.

Figure 15:
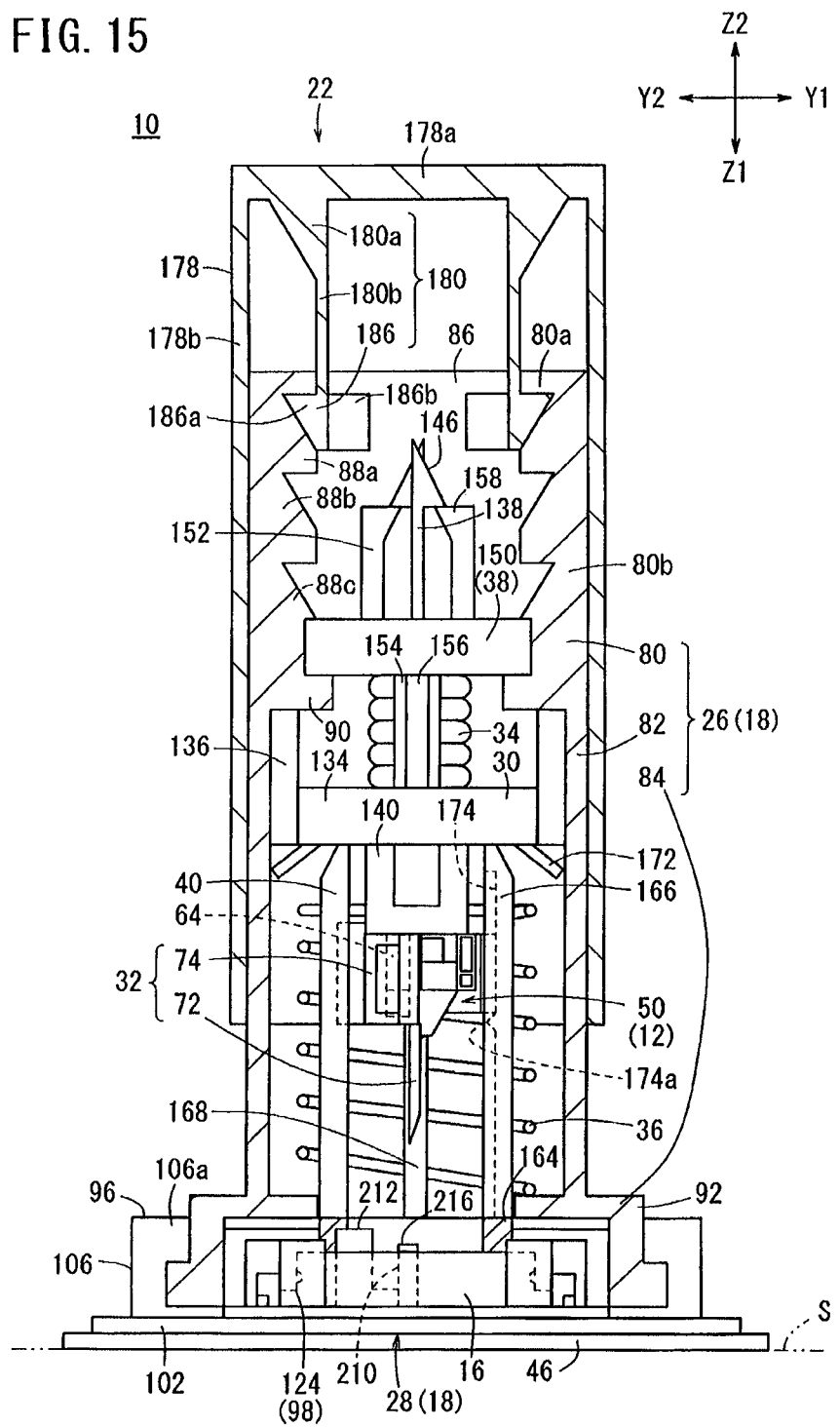
FIG. 15 is a partial front cross-sectional view illustrating a first state before the inserting operation of the sensor unit and the insertion needle.

FIG. 15 illustrates a first state of the sensor inserting device before the inserting operation of the sensor unit 50 and the insertion needle 32.

At a state in which the sensor inserting device 10 is positioned on the skin S of the patient, the operating bar 180 of the push handle 22 is positioned at the uppermost of the internal space 86 of the housing 26 as illustrated in FIG. 15. Further, the sensor inserting device 10 is in the first state in which the sensor unit 50 and the insertion needle 32 are supported by the head 30 at a position spaced from the distal end portion of the device body 18 by a predetermined distance (at an approximately middle portion (intermediate portion) in the housing 26).

In this state, regarding the head 30, the pair of head side arms 138 is engaged with the pair of fixing member side arms 152 of the fixing member 38. Further, the advance spring 34 is compressed between the elliptical plate 134 of the head 30 and the middle disk 150 of the fixing member 38. Further, as for the guiding member 40, the guiding member side hooks 176 (see FIG. 10A) are engaged with the fixing member side hooks 162 (see FIG. 9C) of the fixing member 38 and hand toward the distal end side.

Figure 19A:
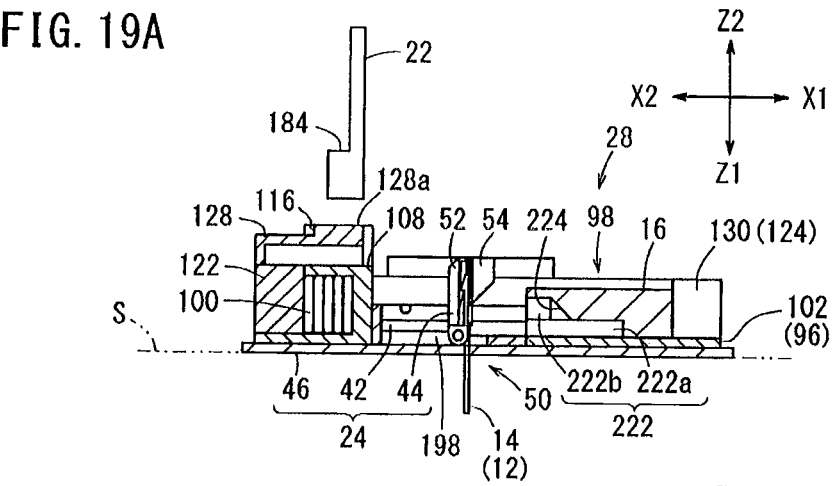
FIG. 19A is a side cross-sectional view specifically illustrating a state before the sliding operation of the transmitter.

Further, in the first state, as for the slider mechanism 28 attached to the distal end portion of the sensor inserting device 10, the slider side connecting portion 122 of the slider 98 is positioned close to the rear wall 108 of the slider mechanism body 96, and the slider controlling plate 128 of the slider 98 is engaged with the slider engaging portion 116, so that the slider spring 100 is in a compressed state (see FIG. 19A). Further, the dwelling member 24 is supported by the ribs 132 of the slider 98 so that the dwelling member 24 is arranged above the dwelling member window 104. The transmitter 16 is located adjacent to the dwelling member 24 (the transmitter arrangement portion 120), and the side surface and a portion of the front surface of the transmitter 16 are surrounded by the support arm 124 of the slider 98.

Further, the sensor unit 50 and the insertion needle 32 are positioned, above the dwelling member 24, where the distal end portion of the head 30 is attached. In this state, the sensor side hook 64 (also see FIG. 5) of the sensor 12 and the engaging arm side hook 216 of the dwelling member 24 face each other. Further, as for the sensor unit 50, the sensor side guiding portion 62 is temporarily engaged with the temporary-engaging protrusion 174a of the guiding member 40 so that careless dropping of the sensor unit 50 toward the distal end side is prevented. From the first state, the inserting operation of the sensor unit 50 and the insertion needle 32 by the sensor inserting device 10 is carried out.

Figure 16:
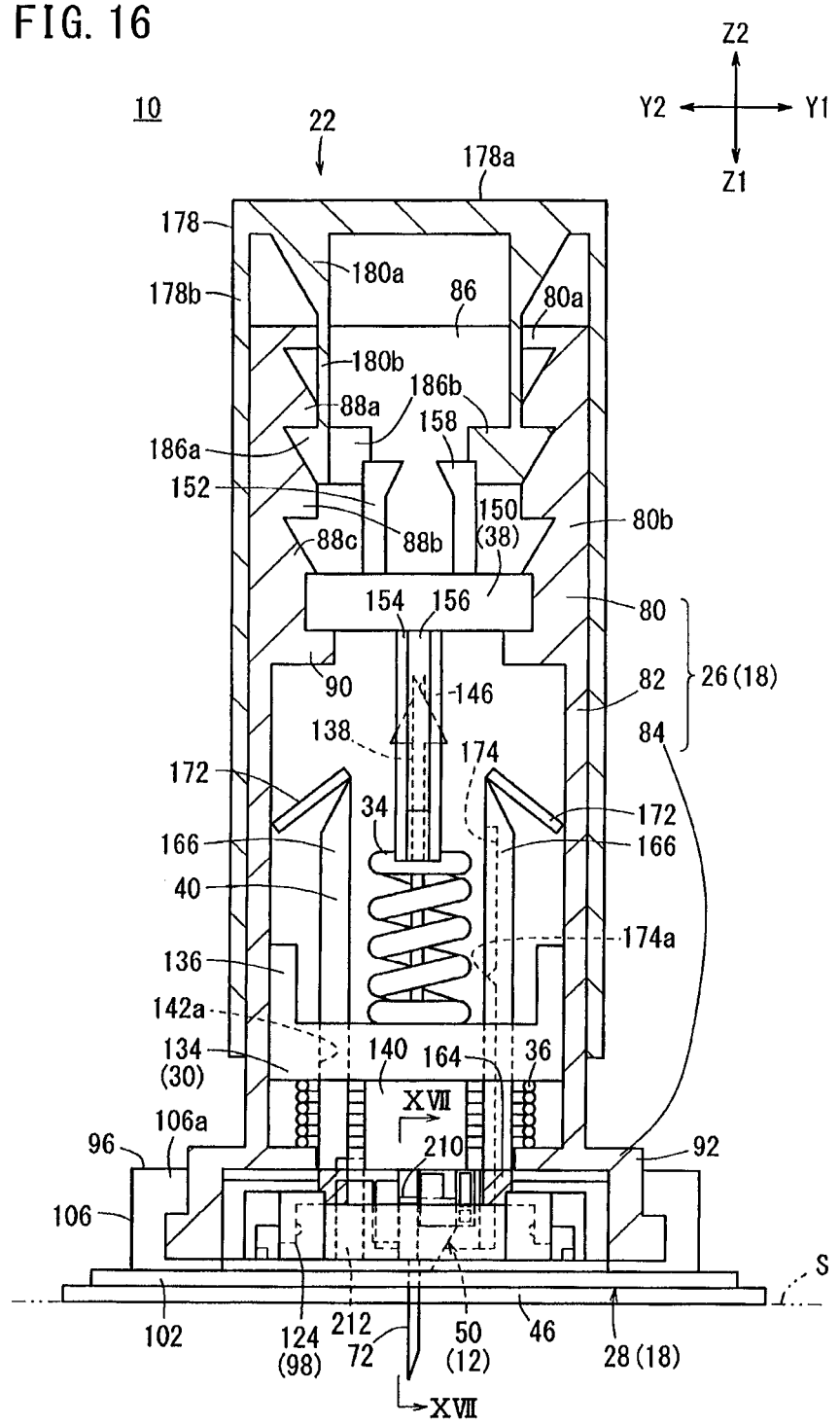
FIG. 16 is a partial front cross-sectional view illustrating a second state in which the sensor unit and the insertion needle are inserted in the skin of a patient.
Figure 17:
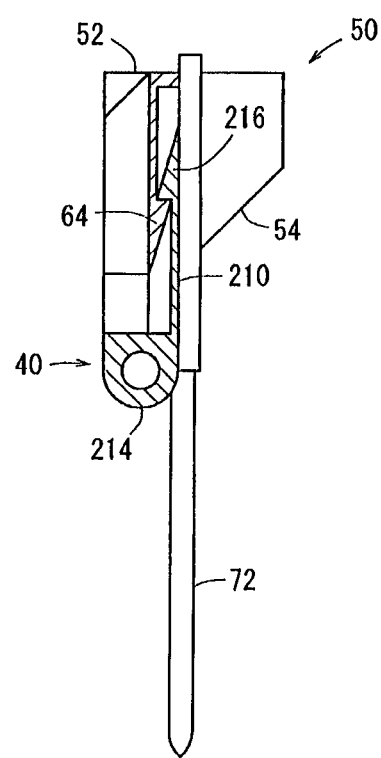
FIG. 17 is a cross-sectional view taken along the section line XVII-XVII in FIG. 16.

FIGS. 16 and 17 illustrate a second state in which the sensor unit 50 and the insertion needle 32 are inserted in the skin S of a patient.

When the inserting operation of the sensor unit 50 and the insertion needle 32 is carried out, the user of the sensor inserting device 10 grips the push handle 22 with one hand and pushes the push handle 22 toward the distal end direction (Z1 direction). In this manner, the first stage displacement of the operating bar 180 of the push handle 22, in which the operating bar 180 goes over the first tooth 88a of the housing 26, is carried out. When the first stage displacement of the push handle 22 is carried out, the operating bar 180 is guided by the first tooth 88a to deflect inward so as to move the contact portion 186b inward, thereby pushing the head side hook 146 of the head side arm 138 inward. As a result, the engagement of the head side arm 138 and the fixing member side arm 152 is released.

By the releasing of the engagement, the compressed advance spring 34 expands so as to strongly push out the head 30 toward the distal end direction. In this manner, the sensor 12 (sensor unit 50) and the insertion needle 32 attached to the distal end portion of the head 30 move toward the distal end direction with the head 30 and the sensor unit 50 and the insertion needle 32 are inserted in the skin S of the patient facing the distal end portion of the sensor inserting device 10. During the movement of the head 30, the sensor unit 50 and the insertion needle 32 are guided by the arm groove 174 of the first guide arm 166. Further, the head 30 can be moved toward the distal end direction without tilting the sensor unit 50 and the insertion needle 32 since the extending portion 82 guides the head side guide 136 and also the first and second guide arms 166 and 168 guide the first and second head side inserting holes 142*a* and 142*b*. During the movement of the head 30, swingably engaging plate 172 of the first guide arm 166 swings toward the closing direction (direction toward the first guide arm 166) by contacting the first head side inserting hole 142*a* so as to allow the head 30 to pass.

By virtue of the inserting operation described above, the state of the sensor inserting device 10 changes to the second state in which the detector 14 of the sensor 12 is inserted into the body of the patient at the location of insertion, that is, the distal end of the device. In the second state, when the sensor unit 50 and the engaging arm 44 are viewed from the side surface direction (see FIG. 17), the sensor side hook 64 is engaged with the engaging arm side hook 216. That is, by the moving force toward the distal end direction of the sensor unit 50, the engaging arm side hook 216 of the engaging arm 44 which is in the upright position enters into the sensor side hook 64. As a result, the engaging arm 44 supports the sensor unit 50 at the location of insertion (i.e., the engaging arm 44 holds the sensor unit 50 at the insertion position).

Further, in the second state, the return spring 36 arranged on the distal end side of the head 30 is compressed by the movement of the head 30 toward the distal end direction. By compression of the return spring 36, the moving force of the head 30 toward the distal end direction is absorbed, so that a suitable force for the insertion needle 32 to pierce the skin S of the patient is provided.

Figure 18:
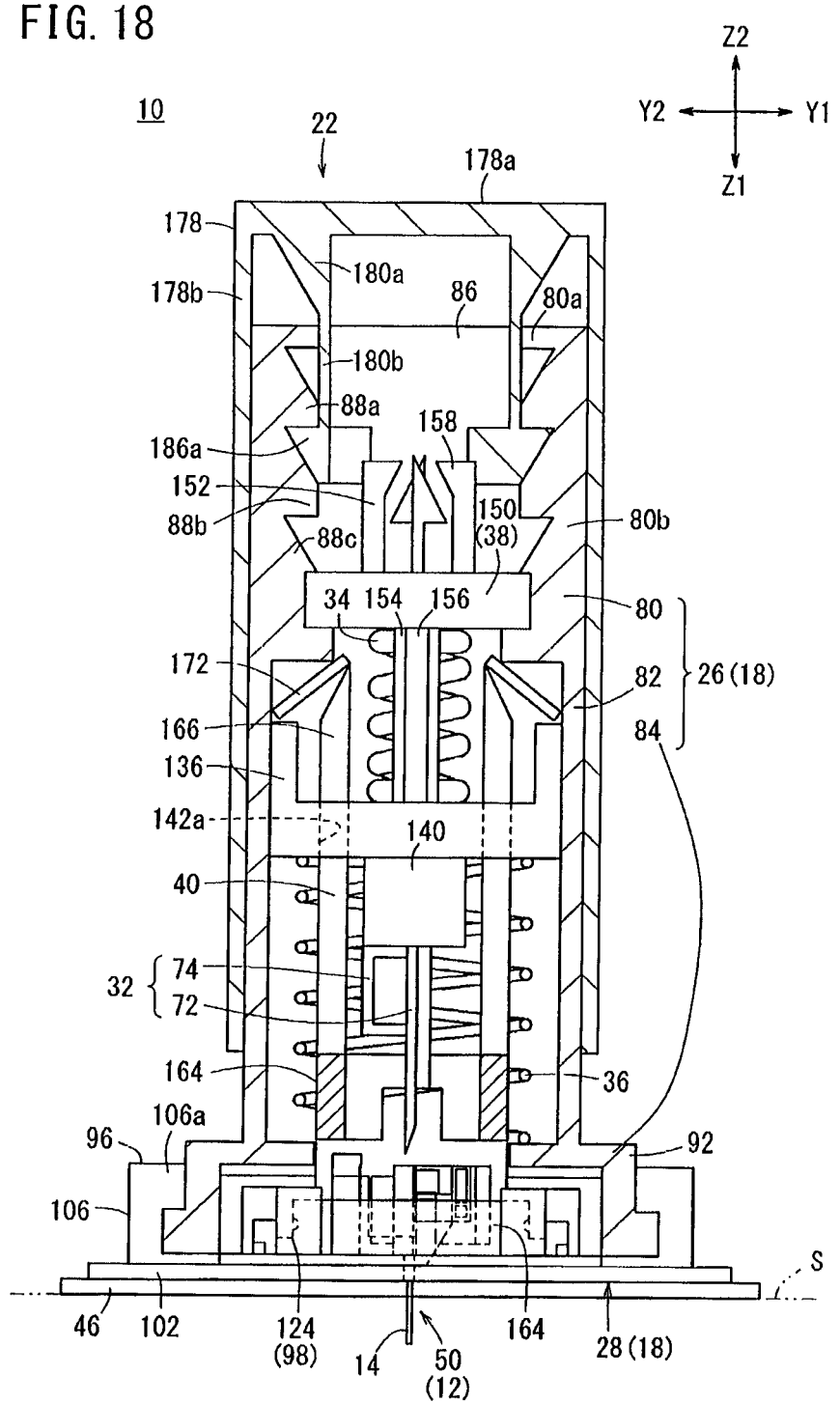
FIG. 18 is a partial front cross-sectional view illustrating a third state in which the insertion needle is separated from the sensor.

FIG. 18 illustrates a third state in which the insertion needle 32 is separated from the sensor 12.

After changing to the second state, the state of the sensor inserting device 10 changes to the third state as illustrated in FIG. 18. That is, in the sensor inserting device 10, the return spring 36 compressed in the second state then expands to move the head 30, which has moved toward the distal end direction, toward the proximal end direction. In the process, the insertion needle 32 is pulled back toward the proximal end direction along with the movement of the head 30. However, the sensor unit 50 which has been temporarily held by the insertion needle 32 is kept in a state supported by the dwelling member 24 (a state in which the sensor side hook 64 is engaged with the engaging arm side hook 216).

Therefore, in the third state, the sensor unit 50 continues to dwell at the location of insertion and the insertion needle 32 is separated from the sensor unit 50. In this case, the sensor unit 50 is supported in the dwelling member 24 in the upright position by the engaging arm 44.

Further, when the head 30 moves toward the proximal end direction, the swingably engaging plate 172 of the guiding member 40 makes contact with the head side guide 136 so that the moving force toward the proximal end direction is transmit from the head 30 to the guiding member 40, thereby moving the guiding member 40 toward the proximal end direction with the head 30. Therefore, in the third state, the guiding member 40 is separated from the slider mechanism 28 in the sensor inserting device 10.

Figure 19B:
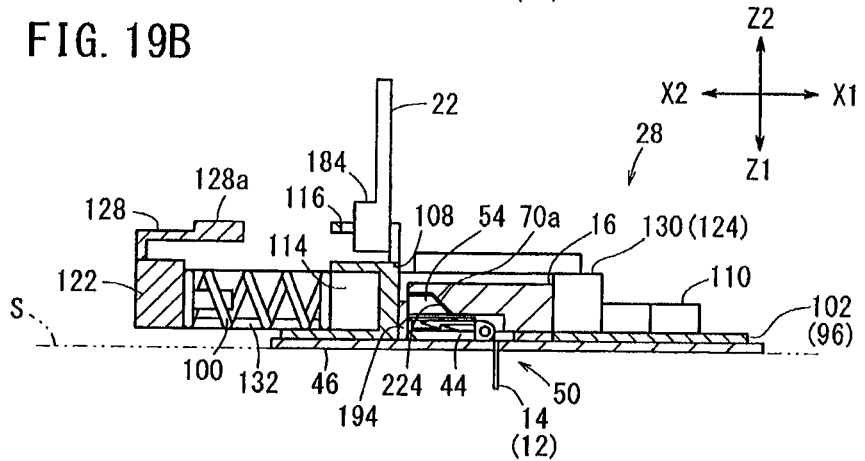
FIG. 19B is a side cross-sectional view illustrating a fourth state after the sliding operation of the transmitter.
Figure 19C:
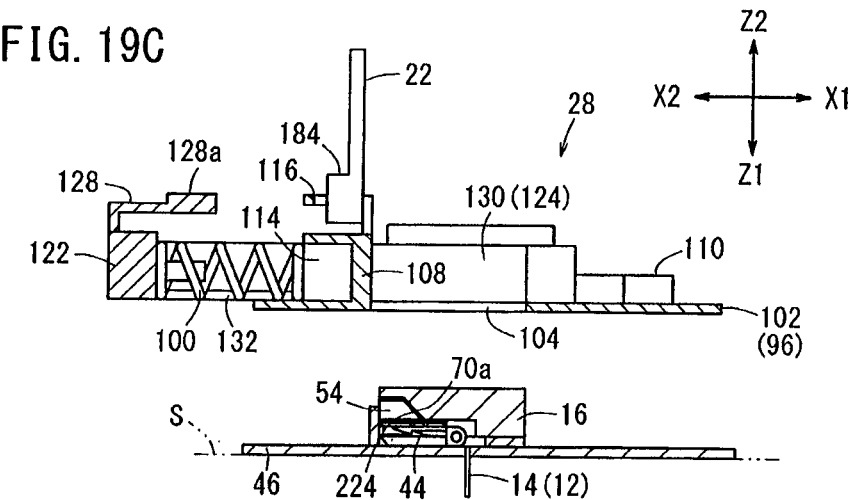
FIG. 19C is a side cross-sectional view illustrating a state in which the sensor inserting device is separated from the skin of the patient.

FIG. 19A illustrates a state before the sliding operation of the transmitter 16, FIG. 19B illustrates a fourth state after the sliding operation of the transmitter 16, and FIG. 19C illustrates a state in which the sensor inserting device 10 is separated from the skin of the patient.

After the third state, the state of the sensor inserting device 10 changes, by slidably moving the transmitter 16, to the fourth state in which the sensor unit 50 and the transmitter 16 are connected. Note that, in the sensor inserting device 10, the device body 18 and the dwelling member 24 are connected via the rib 132 so that the sensor inserting device 10 cannot be separated from the skin S until the supporting of the dwelling member 24 by the rib 132 is cancelled. Therefore, detachment of the sensor inserting device 10 in a state without connection to the transmitter 16 can be prevented. The supporting of the dwelling member 24 by the rib 132 can be cancelled by the sliding movement of the transmitter 16.

In this case, the push handle 22 gripped by the user is further operated to push toward the distal end direction (Z1 direction). In this manner, the second stage displacement of the operating bar 180 of the push handle 22, in which the operating bar 180 goes over the second tooth 88*b* of the housing 26, is carried out. During the second stage displacement of the push handle 22, the operating bar 180 is guided by the second tooth 88*b* so as to deflect inward. Since the contact portion 186*b* is formed to be offset from the arrangement of the fixing member side arm 152 of the fixing member 38, the operating bar 180 can deflect without touching the fixing member side arm 152, thereby allowing the push handle 22 to displace easily.

As illustrated in FIG. 19A, in the sensor inserting device 10, in the first to third states, the push handle side pressing plate 184 of the push handle 22 is located above the slider controlling plate 128 of the slider mechanism 28. In this state, when the second stage displacement of the push handle 22 is carried out, as illustrated in FIG. 19B, the push handle side pressing plate 184 formed in the lower portion of the push handle 22 can push in the slider controlling plate 128. Then, the engagement of the slider controlling plate 128 of the slider 98 and the slider engaging portion 116 of the slider mechanism body 96 is released, and thereby the slider 98 slidably moves toward the rear direction by the pressing force of the slider spring 100.

Along with the sliding movement of the slider 98, the transmitter 16 supported by the support arm 124 (slider side hook 130) moves toward the rear direction. Thereby, the transmitter 16 is inserted in the base 42 from the front side and moves, guided by the supporting groove 200, until contact with the rear wall 108 is made.

By the movement of the transmitter 16, the sensor unit 50 and the engaging arm 44 which have been in the upright position at an approximately middle location of the base 42 contacts the transmitter 16 and are pressed to fall down. That is, the engaging arm 44 rotates about the bearing 214 and falls down rearward by contacting the transmitter 16. The sensor unit 50 also falls down rearward by contacting the transmitter 16, bending the connecting portion 56*a* of the sensor base 56. In this process, the engaging arm 44 falls down into the containing hole 198 so as to be contained in the containing hole 198. The engaging plate thus moves from the vertically oriented upstanding position to the horizontally oriented fall down position.

Further, the sensor unit 50 which is made to fall down by the transmitter 16 enters into the connecting terminal recess 222 along with the sliding movement of the transmitter 16. That is, the sensor 12 and the engaging member 52 are contained in the first space 222*a*, and the connecting member 54 is contained in the second space 222*b*. In this state, since the second space 222*b* is formed in a tapered shape, the connecting member 54 can easily be introduced into the second space 222*b*. Further, in a state when the transmitter 16 is inserted in the base 42, the tapered surface (conductive terminal) of the connecting member 54 is connected to the tapered surface 224 (conductive connecting surface) inside the second space 222*b* so that the blood sugar level (current value) detected by the sensor 12 can surely be transmitted to the transmitter 16.

Further, in a state when the transmitter 16 is inserted in the base 42, the rib 132 which has supported the dwelling member 24 is separated from the guiding groove 202, thereby cancelling the supporting state. Therefore, as illustrated in FIG. 19C, the dwelling member 24 (including the sensor unit 50 and the transmitter 16) can be taken out from or can pass through the dwelling member window 104 of the slider mechanism body 96. In this manner, the sensor inserting device 10 allows the sensor unit 50 and the transmitter 16 to dwell on the skin S of the patient while the remainder of the sensor inserting device 10 is separated from the sensor unit 50 and the transmitter 16.

As described above, the sensor inserting device 10 according to the embodiment disclosed here by way of example provides the insertion of the detector 14 of the sensor 12 into the body of the patient by the movement mechanism 20 and the connection between the sensor 12 and the transmitter 16 at the location of insertion, and allows the sensor 12 and the transmitter 16 to dwell on the skin S of the patient. Consequently, the connection between the sensor unit 50 and the transmitter 16 which are to dwell on the skin S of the patient need not be carried out manually, so that the insertion and dwelling of the sensor 12 can be carried out within a shorter time, thereby reducing suffering of the patient.

Further, since the dwelling member 24 is attached to the sensor 12 by the movement of the sensor unit 50 caused by the movement mechanism 20, the sensor 12 can be attached to the dwelling member 24 without effort. The sensor inserting device 10 thus provides further efficient operation of the insertion and dwelling of the sensor 12.

Further, by the dwelling member 24 supporting (engaging) the sensor unit 50 by the engaging arm 44 and the base 42 supporting the sensor unit 50 in a state connected to the transmitter 16, further firm connection of the sensor unit 50 and the transmitter 16 on the skin S of the patient is provided, thereby providing stable and continuous detection of biological information by the sensor 12.

In this case, by the slider mechanism 28 allowing the transmitter 16 to slide toward the base 42 so that the transmitter 16 is inserted, and supported by the dwelling member 24, the connection between the sensor unit 50 and the transmitter 16 is rather easily carried out.

Further, by a relatively simple operation of the two-stage displacement of the push handle 22 toward the distal end direction of the device body 18, the sensor inserting device 10 inserts the detector 14 of the sensor 12 into the body of the patient and further allows the sensor base 56 of the sensor 12 and the transmitter 16 to be connected with each other and dwell on the skin S of the patient.

The above description of the operation of the sensor inserting device 10 describes the two-stage displacement of the push handle 22 in a stagewise manner. However, the user can carry out the displacement of the push handle 22 continuously without stopping the operation between the first stage and the second stage. That is, the user can change the state of the sensor inserting device 10 from the first stage through the fourth stage by a single-push operation of the push handle 22.

Further, by including the safety mechanism 226, the sensor inserting device 10 can rather surely prevent trouble of carelessly moving the sensor unit 50 and the insertion needle 32 toward the distal end direction and piercing with the insertion needle 32.

The detailed description above describes a sensor inserting device and method disclosed by way of example. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An operating method of a sensor inserting device comprising:
   supporting both a sensor which measures biological information and an insertion needle at a location proximally spaced a predetermined distance from a distal end portion of a device body of the sensor inserting device, the sensor including a detector which detects a body fluid component of a patient used to measure the biological information, and the sensor inserting device including a signal processor which processes a signal including biological information output from the sensor, the signal processor being attached to the device body and electrically disconnected from the sensor;
   moving the sensor and the insertion needle, which are supported at the location proximally spaced from the distal end portion of the device body, toward a distal end direction so that the detector of the sensor and a portion of the insertion needle protrude distally beyond a distal end portion of the device body;
   after the detector and the portion of the insertion needle are positioned distally beyond the distal end portion of the device body, separating the insertion needle from the sensor by moving the insertion needle relative to the sensor toward a proximal end direction; and
   electrically connecting the sensor and the signal processor by operation of the device body after the insertion needle is separated from the sensor.

2. The operating method according to claim 1, wherein the moving of the sensor and the insertion needle toward the distal end direction so that the detector and the portion of the insertion needle protrude distally beyond the distal end portion of the device body is accomplished by pushing a push handle of the sensor inserting device toward the distal end direction.

3. The operating method according to claim 1, further comprising positioning a distal end of the sensor inserting device adjacent skin of the patient before moving the sensor and the insertion needle toward the distal end direction, and wherein the moving of the sensor and the insertion needle toward the distal end direction includes penetrating the skin of the body with the insertion needle at a location of insertion and thereafter inserting the detector into the skin at the location of insertion.

4. The operating method according to claim 1, further comprising adhering a distal end of the sensor inserting device to skin of the patient before moving the sensor and the insertion needle toward the distal end direction, and wherein the moving of the sensor and the insertion needle toward the distal end direction includes penetrating the skin of the body with the insertion needle at a location of insertion and thereafter inserting the detector into the skin at the location of insertion, the penetration of the skin with the insertion needle occurring while the distal end of the sensor inserting device is adhered to the skin of the patient.

5. The operating method according to claim 1, wherein the sensor is a part of a sensor unit that also includes an engagement member, the movement of the sensor toward the distal end direction including moving the sensor unit in the distal end direction, and wherein the separation of the insertion needle from the sensor includes engaging the engagement member of the sensor unit with an engaging arm of the sensor inserting device while the sensor unit is moving in the distal end direction and applying a force to the insertion needle toward the proximal end direction after the engagement member has engaged the engaging arm.

6. A method comprising:
moving a sensor inserting device toward skin of a living body, the sensor inserting device comprising an insertion needle, a sensor which measures biological information and outputs the biological information, and a signal processor, the moving of the sensor inserting device toward the skin of the living body including moving the insertion needle, the sensor and the signal processor toward the skin of the living body;
positioning a distal end of the sensor inserting device against the skin of the living body, the needle possessing a distal end that is proximally spaced from the distal end of the sensor inserting device when the distal end of the sensor inserting device is initially positioned against the skin of the living body, the sensor including a detector which detects a body fluid component of the living body used to measure the biological information;
moving both the sensor and the insertion needle toward the skin of the living body to cause the distal end of the insertion needle to puncture the skin of the living body, the movement of the sensor resulting in movement of the detector to position at least a part of the detector in the skin of the living body;
during the moving of both the sensor and the insertion needle toward the skin of the living body, the sensor being electrically disconnected from the signal processor which processes the biological information output from the sensor;
after the puncturing of the skin of the living body, moving the insertion needle away from the skin of the living body to remove the distal end of the insertion needle from the skin of the living body while keeping the at least a part of the detector in the skin of the living body; and
electrically connecting, after the insertion needle is removed from the skin of the living body, the sensor to the signal processor which processes the biological information output from the sensor.

7. The method according to claim 6, wherein the moving of both the sensor and the insertion needle toward the skin of the living body comprises applying a force to a push handle to release an engagement that prevents a spring force from being applied to the insertion needle and the sensor, the release of the engagement causing the spring force to be applied to the sensor and the insertion needle to cause the movement of the sensor and the insertion needle toward the skin of the living body.

8. The method according to claim 6, wherein the moving of the sensor and the insertion needle toward the skin of the living body is accomplished by applying an axial pushing force to a push handle of the sensor inserting device.

9. The method according to claim 6, wherein the insertion needle punctures the skin of the patient at a location of insertion, and further comprising inserting the detector into the skin at the location of insertion after puncturing the skin of the patient at the location of insertion.

10. The method according to claim 6, further comprising adhering a distal end of the sensor inserting device to the skin of the living body before moving the sensor and the insertion needle toward the skin of the living body, and wherein the moving of the sensor and the insertion needle toward the skin of the living body includes penetrating the skin of the living body with the insertion needle at a location of insertion and thereafter inserting the detector into the skin of the living body at the location of insertion, the penetration of the skin of the living body with the insertion needle occurring while the distal end of the sensor inserting device remains adhered to the skin of the living body.

11. The method according to claim 6, wherein the insertion needle and the sensor are connected to one another so that the insertion needle and the sensor move together toward to the skin of the living body, and the moving of the insertion needle away from the skin of the living body to remove the distal end of the insertion needle from the skin of the living body includes separating the insertion needle from the sensor.

12. The method according to claim 11, wherein the sensor is a part of a sensor unit that also includes an engagement member, the movement of the sensor toward the skin of the living body including moving the sensor unit toward the skin of the living body, and wherein the separating of the insertion needle from the sensor includes engaging the engagement member of the sensor unit with an engaging arm of the sensor inserting device while the sensor unit is moving toward the skin of the living body and applying a force to the insertion needle toward in a direction away from the skin of the living body after the engagement member has engaged the engaging arm.

13. The method according to claim 6, wherein the electrical connection of the sensor to the signal processor includes rotating the sensor and moving the signal processor so that at least a part of the signal processor overlies at least a part of the sensor.

14. The method according to claim 6, wherein the electrical connection of the sensor to the signal processor includes moving the signal processor towards the sensor so that the movement of the signal processor towards the sensor causes the sensor to rotate, followed by the electrical connection of the sensor to the signal processor.

15. The method according to claim 6, wherein during the moving of both the sensor and the insertion needle toward the skin of the living body, the signal processor is slidably positioned on a body base of the sensor inserting device, the body base resting on the skin of the living body while the insertion needle is puncturing the skin of the living body, the electrical connection of the sensor to the signal processor including sliding the signal processor toward the sensor.

16. The method according to claim 15, wherein during the moving of both the sensor and the insertion needle toward the skin of the living body, the sensor is positioned in a through window of the body base and is adhered to the skin of the living body.

17. The method according to claim 6, wherein the electrical connection of the sensor to the signal processor includes applying a spring biasing force to the signal processor to move the signal processor towards the sensor.

18. The method according to claim 6, wherein the relatively moving of the sensor and the signal processor moves the sensor and the signal processor from a position spaced apart from one another to a position in which the conductive connecting surface and the conductive portion overlie one another.

19. An operating method of a sensor inserting device comprising:
- supporting both a sensor which measures biological information and an insertion needle at a location proximally spaced a predetermined distance from a distal end portion of a device body of the sensor inserting device, the sensor including a detector which detects a body fluid component of a patient used to measure the biological information, and the sensor inserting device including a signal processor which processes a signal including biological information output from the sensor and transmits the biological information outside the sensor inserting device;
- moving the sensor and the insertion needle, which are supported at the location proximally spaced from the distal end portion of the device body, toward a distal end direction so that the detector of the sensor and a portion of the insertion needle protrude distally beyond a distal end portion of the device body, the signal processor being movably mounted on the device body while the sensor and the insertion needle are moved toward the distal end direction;
- after the detector and the portion of the insertion needle are positioned distally beyond the distal end portion of the device body, separating the insertion needle from the sensor by moving the insertion needle relative to the sensor toward a proximal end direction; and
- moving the signal processor relative to the sensor, after the insertion needle is separated from the sensor, to bring a conductive connecting surface of the signal processor into electrical connection with a conductive portion of the sensor to convey the signal output from the sensor to the signal processor.

20. The method according to claim 19, wherein the device body includes a user-operable handle, the moving of the sensor and the insertion needle toward the distal end direction being accomplished by operating the handle, and the relatively moving of the sensor and the signal processor being accomplished by operating the handle.

* * * * *